US011813236B2

(12) United States Patent
Mardinoglu et al.

(10) Patent No.: US 11,813,236 B2
(45) Date of Patent: *Nov. 14, 2023

(54) SUBSTANCES FOR TREATMENT OF FATTY LIVER-RELATED CONDITIONS

(71) Applicant: SCANDIBIO THERAPEUTICS AB, Johanneshov (SE)

(72) Inventors: Adil Mardinoglu, Gothenburg (SE); Jan Borén, Gothenburg (SE); Mathias Uhlén, Lidingö (SE)

(73) Assignee: SCANDIBIO THERAPEUTICS AB, Johanneshov (SE)

( * ) Notice: Subject to any disclaimer, the term of this patent is extended or adjusted under 35 U.S.C. 154(b) by 38 days.

This patent is subject to a terminal disclaimer.

(21) Appl. No.: 17/471,780

(22) Filed: Sep. 10, 2021

(65) Prior Publication Data

US 2021/0401787 A1 Dec. 30, 2021

Related U.S. Application Data

(63) Continuation of application No. 16/471,220, filed as application No. PCT/SE2017/051306 on Dec. 20, 2017, now Pat. No. 11,141,396.

(30) Foreign Application Priority Data

Dec. 22, 2016 (SE) .................................. 1651735-1

(51) Int. Cl.
| A61K 31/198 | (2006.01) |
| A61P 1/16 | (2006.01) |
| A61K 31/205 | (2006.01) |
| A61K 31/706 | (2006.01) |

(52) U.S. Cl.
CPC .......... *A61K 31/198* (2013.01); *A61K 31/205* (2013.01); *A61K 31/706* (2013.01); *A61P 1/16* (2018.01)

(58) Field of Classification Search
None
See application file for complete search history.

(56) References Cited

U.S. PATENT DOCUMENTS

| 5,798,265 A | 8/1998 | Springer et al. |
| 2005/0176144 A1 | 8/2005 | Odaly |
| 2007/0286909 A1 | 12/2007 | Smith et al. |
| 2018/0071273 A1 | 3/2018 | Horn |

FOREIGN PATENT DOCUMENTS

| JP | 2016516040 A | 6/2016 | |
| JP | 6303979 B2 | 4/2018 | |
| WO | 9402036 A1 | 2/1994 | |
| WO | 0228379 A2 | 4/2002 | |
| WO | 03006072 A1 | 1/2003 | |
| WO | 2013052117 A1 | 4/2013 | |
| WO | 2014152016 A1 | 9/2014 | |
| WO | 2014159684 A1 | 10/2014 | |
| WO | 2016149277 A1 | 9/2016 | |
| WO | 2016191468 A1 | 12/2016 | |
| WO | WO-2016191468 A1 * | 12/2016 | ........... A61K 31/197 |
| WO | 2017059895 A1 | 4/2017 | |

OTHER PUBLICATIONS

"International Search Report and Written Opinion corresponding to International Application No. PCT/SE2017/051306 dated Feb. 22, 2018".
"Office Action corresponding to Japanese Application No. 2019-534862 dated Jul. 1, 2021".
El-Lakkany, Naglaa , et al., "Co-administration of metformin and N-acetylcysteine with dietary control improves the biochemical and histological manifestations in rats with non-alcoholic fatty liver.", Research in pharmaceutical sciences, 11(5):374-382 (Oct. 2016).
Kawanaka, Masonori , et al., "Nutritional requirements of Schistosoma japonicum eggs.", The Journal of parasitology, 69(5):857-861. (Oct. 1983).
Lim, Chae Young, et al., "Effects of carnitine on peripheral blood mitochondrial DNA copy number and liver function in non-alcoholic fatty liver disease.", The Korean Journal of Gastroenterology, 55(6)384-389 (2010).

(Continued)

Primary Examiner — Dale R Miller
(74) Attorney, Agent, or Firm — Myers Bigel, P.A.

(57) ABSTRACT

There is provided a composition comprising: A) serine, glycine, betaine, N-acetylglycine, N-acetylserine, dimethylglycine, sarcosine and/or phosphoserine; B) N-acetyl cysteine, cysteine and/or cystine; C) optionally carnitine, deoxycarnitine, gamma-butyrobetaine, 4-trimethylammnoniobutanal, 3-hydroxy-N6,N6,N6-trimethyl-L-lysine, N6,N6,N6-trimethyl-L-lysine and/or lysine; and D) nicotinamide riboside, quinolinate, deamino-NAD+, nicotinate D-ribonucleotide, nicotinamide D-ribonucleotide, nicotinate D-ribonucleoside, nicotinamide and/or nicotinate, wherein the molar ratio of A) to D) is between 250:1 and 1.5:1 and the molar ratio of A) to B) is between 16:1 and 1:4. The composition may be used in a method of treatment of a medical condition selected from the group consisting of non-alcoholic fatty liver disease (NAFLD), alcoholic fatty liver disease (AFLD), type 2 diabetes, obesity, insulin resistance and dyslipidemia.

21 Claims, 7 Drawing Sheets

(56) References Cited

OTHER PUBLICATIONS

Mardinoglu, et al., ""Personal model-assisted identification of NAD+ and glutathione metabolism as intervention target in NAFLD", Molecular Systems Biology 13(3):916 (2017) (17 pages)".
Mardinoglu, Adil, et al., "Genome-scale metabolic modelling of hepatocytes reveals serine deficiency in patients with non-alcoholic fatty liver disease.", Nature communications, 5(1):1-11. (Year:2014).
Marzocchi, et al., ""Treatment of non-alcoholic fatty liver disease: State of the art", Gatroenterology International 16(1-2):9-16 (2003)".
Wang, P, et al., "Hepatic NAD-+ deficiency as a therapeutic target for NAFLD in aging.", Chinese Journal of Pharmacology and Toxicology, (10), 142. (Year: 2016).
Yang, Hong, et al., "Combined Metabolic Activators Decrease Liver Steatosis by Activating Mitochondrial Metabolism in Hamsters Fed with a High-Fat Diet", Biomedicines 9:1440 (Oct. 11, 2021) 22 pages.

* cited by examiner

SUBSTANCES FOR TREATMENT OF FATTY LIVER-RELATED CONDITIONS

STATEMENT OF PRIORITY

This application is continuation of and claims priority to U.S. patent application Ser. No. 16/471,220, filed Jun. 19, 2019, now allowed, which is a 35 U.S.C. § 371 national phase application of PCT Application No. PCT/SE2017/051306 filed Dec. 20, 2017, which claims priority to Swedish Application No. 1651735-1 filed Dec. 22, 2016, the entire contents of each of which is incorporated by reference herein.

TECHNICAL FIELD

The invention relates to treatment of fatty liver diseases and related disorders.

BACKGROUND

Hepatic steatosis (HS) is defined as the accumulation of fat in liver with no evidence of hepatocellular injury and it is the most common chronic liver disease worldwide (Vetelainen et al, 2007). HS is the characteristic feature of non-alcoholic fatty liver disease (NAFLD) and it is strongly associated with obesity, insulin resistance, type 2 diabetes (T2D) and cardiovascular diseases (Ratziu et al, 2010). Up to 30% of subjects with NAFLD develop non-alcoholic steatohepatitis (NASH), which is a serious illness in which inflammation and scarring eventually can lead to cirrhosis and hepatocellular carcinoma (HCC) (Dyson et al, 2014).

The underlying molecular mechanisms leading to the occurrence of HS and its transition to severe liver disorders remain elusive, which limits the identification of drug targets and discovery of biomarkers that may be used to design effective treatment strategies.

SUMMARY

There are currently few pharmaceutical treatments for HS and its associated clinical conditions (Machado & Cortez-Pinto, 2012) and the present inventors have realized that an integrative systems biology-based approach may help to address these significant unmet medical needs. In this context, genome-scale metabolic models (GEMs) can be used to gain more insights about the molecular mechanisms involved in the occurrence of HS and associated disorders, and in turn may enable therapeutic discoveries. GEMs are the collection of biochemical reactions that are known to occur in particular cells/tissues and these models have been used in the integration of cellular, physiological and clinical data to reveal the underlying molecular mechanisms of metabolism-related disorders.

The present inventors have designed treatment strategies for NAFLD based on an understanding of the pathophysiology of dyslipidemia. The GEM iHepatocytes2322 contains extensive information about lipid metabolism (Mardinoglu et al, 2014), which is necessary for studying the effect of excess amount of lipids on the underlying molecular mechanism of NAFLD. This GEM can thus be used as a platform for studying the kinetics of lipoproteins and their potential effect on liver metabolism.

To clarify the underlying metabolic disturbances in NAFLD, the present inventors have investigated the metabolic differences in liver between subjects with varying degrees of HS by studying the kinetics of lipid metabolism, taking into account interactions between the liver, adipose, muscle and other peripheral tissues as well as red blood cells. Using personalized genome-scale metabolic modelling, the present inventors elucidated an underlying molecular mechanism of NAFLD and used it in the development of a treatment strategy.

Subjects with varying degrees of HS were characterized and VLDL kinetics were measured. Subsequently, the VLDL kinetic data was integrated with additional experimentally derived flux data to simulate the liver metabolism of each subject using a liver GEM. Then the correlations between the predicted intracellular fluxes of the liver and HS was assessed to detect metabolic derangements in NAFLD. A systems level analysis indicated that altered NAD+ and GSH metabolism (with increased demand for NAD and GSH) was a prevailing feature in NAFLD. Hence, it was postulated that subjects with NAFLD have reduced de novo synthesis of GSH, possibly due to limited availability of glycine in the fasting state. An analysis of plasma metabolomics showed that plasma levels of glycine as well as serine, betaine and N-acetylglycine (which can be converted to glycine) were lower in subjects with high HS compared to those with low HS. Moreover, analysis of the metabolomics data revealed significant negative correlations between the plasma levels of glycine, serine, betaine and N-acetylglycine with HS. In a mouse study it was showed that supplementation of the precursors for NAD and GSH significantly decreased HS. Finally, in a proof-of-concept human study, it was found that HS is significantly decreased whereas markers of liver function are significantly improved in NAFLD patients after supplementation with serine (a precursor to glycine).

Serine derived from a branch of glycolysis can be converted to glycine, which in turn provides carbon units for one-carbon metabolism using THF. It has previously been shown that NAFLD patients and controls have similar folate levels and the present inventors therefore conclude that THF is not likely to be limiting for glycine biosynthesis.

Increased release of free fatty acids (FAs) in the fasting state is a known characteristic of obesity and associated disorders such as NAFLD (Karpe et al, 2011; Nestel & Whyte, 1968). The present inventors have shown that the influx of FAs into the liver with simultaneous low excretion of VLDL (i.e., high net fat influx (NFI)) profoundly affected the fluxes. GSH turnover as well as increased fat oxidation, increased oxidative phosphorylation with subsequent increased demand for oxygen and increased ketogenesis were strongly correlated with high NFI.

The increases in GSH, NAD+, oxidative phosphorylation, oxygen consumption and ketone production are thus all model-predicted demands which would ideally be met for dealing with high HS. If any of these demands cannot easily be met in vivo due to reduced concentrations of the substrates, then cellular health might be compromised. For example, if the predicted demand for GSH in high HS is not met by an increased supply of GSH, then the redox balance could be at risk of being insufficient for normal cellular health in high HS. Indeed the present inventors have shown that the expression of the enzymes involved in the formation of GSH is significantly lower in obese subjects. Considering that the simulations demonstrated the ideal response of the liver to the increased HS, the upregulation of the fat oxidation and the increased availability of the GSH and NAD+ provides a treatment strategy for NAFLD subjects.

The subjects at highest risk of possible metabolic stress in this analysis were subjects with high FA influx and HS, Importantly, HS alone was not the single characteristic that explained higher demand for GSH, meaning a person with high HS is not necessarily at risk. Since metabolic distress was predicted to correlate well with high NFI and FA influx alone, it can therefore be argued that a subject with high HS but low FA influx is not necessarily at risk of disease. In fact, the expansion of lipids droplets in the liver is one way of disposing of excess FAs. Thus, the HS process itself could theoretically serve to decrease metabolic stress in the liver. Similarly, increased VLDL secretion, increased ketone secretion and increased oxidative phosphorylation are all means through which the liver can dispose of excess FAs.

Through systems level analysis in mice, it has been observed that glycine is the limiting substrate for the de novo synthesis of GSH (Mardinoglu et al, 2015). In a recent study comparing germfree and conventionally raised mice, it was shown that the gut microbiota alters the distribution of AAs along the gastrointestinal tract, affecting the bioavailability of free AAs to the host (Mardinoglu et al, 2015b). It has also been shown that microbiota-induced imbalances in the utilization of AAs, particularly serine and glycine, may affect the biological function of the host. Moreover, the presence of a gut microbiota resulted in increased expression of Nnt in the liver, adipose and gastrointestinal tract tissues and a parallel decrease in plasma and liver levels of glycine.

The data of the present disclosure indicate that increased FA release from adipose tissue and decreased. VLDL secretion from the liver elevate the metabolic stress on the liver. Therefore, it is of clinical value to take into account FA release from adipose tissue together with the degree of HS in subjects with HS.

In conclusion, personalized genome-scale metabolic modelling has been used to elucidate molecular mechanisms involved in the progression of NAFLD and the predictions has been validated by generating additional plasma metabolomics data. In addition, proof-of-concept studies in mice and human has shown that supplementation of the precursors for NAD+ and GSH are useful in prevention and treatment of HS.

Given the results of the modelling discussed above, the present inventors have provided a treatment strategy based on the following insights:

To clear fat, such as fat accumulated in the liver, liver cells burn fatty acids by β-oxidation in the mitochondria, L-carnitine can be supplemented to facilitate the transport of fatty acids into the mitochondria. Further, nicotinamide riboside (NR) can be supplemented to accelerate the β-oxidation in the mitochondria, which however produces toxic by-products. The liver cells naturally produce antioxidants that neutralize the toxic by-products. The formation of the antioxidants is limited by the availability of glycine. Accordingly, glycine and/or serine (a precursor to glycine) can be supplemented to increase the formation of the antioxidants. After sufficient supplementation with glycine and/or serine, cysteine becomes limiting for the formation of the antioxidants. Cysteine and/or N-acetyl cysteine (NAC) can thus be supplemented in addition to the glycine and/or serine to further increase the formation of the antioxidants. The supplementations not only enhance the neutralization of the toxic by-products, but also promotes the β-oxidation of the fatty acids.

Considering metabolic pathways, the present inventors have identified the following alternatives to the above-mentioned substances:

| Substance | Alternatives |
| --- | --- |
| serine | glycine, betaine, N-acetylglycine, N-acetylserine, dimethylglycine, sarcosine and/or phosphoserine |
| NAC | cysteine, cystine |
| L-carnitine | deoxycarnitine, gamma-butyrobetaine, 4-trimethylammoniobutanal, 3-hydroxy-N6,N6,N6-trimethyl-L-lysine, N6,N6,N6-trimethyl-L-lysine and/or lysine |
| NR | quinolinate, deamino-NAD+, nicotinate D-ribonucleotide, nicotinamide D-ribonucleotide, nicotinate D-ribonucleoside, nicotinamide and/or nicotinate |

To obtain the therapeutic effect, it is not necessary include all four substances. The inventors have however identified serine (or one or more of its alternatives) as the most important substance and NR (or one or more of its alternatives) as the second most important substance. Further, the inventors have found that the optimal daily molar dose is higher for serine than for NR.

Non-alcoholic fatty liver disease (NAFLD) and type 2 diabetes (T2D) are common conditions that regularly co-exist and can act synergistically to drive adverse outcomes. The presence of both NAFLD and T2D increases the likelihood of the development of complications of diabetes as well as augmenting the risk of more severe NAFLD, including cirrhosis, hepatocellular carcinoma and death.

Fatty liver (hepatosteatosis) is the earliest abnormality in the pathogenesis of non-alcoholic fatty liver disease (NAFLD) and alcoholic fatty liver disease (AFLD) due either to metabolic risk factors associated with insulin resistance and/or metabolic syndrome in the absence of alcohol consumption or to chronic alcohol abuse. When unchecked, both NAFLD and AFLD lead to steatohepatitis, fibrosis, cirrhosis, hepatocellular carcinoma (HCC) and eventual death.

Primary hepatic steatosis in NAFLD is associated with metabolic risk factors reflecting the metabolic syndrome (MS) such as obesity, insulin resistance and/or dyslipidemia in the majority of patients.

The above-mentioned treatment strategy can thus not only be used for NAFLD and ITS, but also for AFLD, type 2 diabetes, obesity, insulin resistance and dyslipidemia.

Accordingly, the following itemized listing of embodiments of the present disclosure is provided:

1. A composition comprising:
A) serine, glycine, betaine, N-acetylglycine, N-acetylserine, dimethylglycine, sarcosine and/or phosphoserine;
B) optionally N-acetyl cysteine, cysteine and/or cystine;
C) optionally carnitine, deoxycarnitine, gamma-butyrobetaine, 4-trimethylammoniobutanal, 3-hydroxy-N6,N6, N6-trimethyl-L-lysine, N6,N6,N6-trimethyl-L-lysine and/or lysine; and
D) nicotinamide riboside, quinolinate, deamino-NAD+, nicotinate D-ribonucleotide, nicotinamide D-ribonucleotide, nicotinate D-ribonucleoside, nicotinamide and/or nicotinate, wherein the molar ratio of A) to D) is between 250:1 and 1.5:1.

2. The composition of item 1, wherein the molar ratio of A) to B) is between 16:1 and 1:4, such as between 12:1 and 1.5:1, preferably between 10:1 and 3:1.

3. The composition of item 1 or 2, wherein the molar ratio of A) to C) is between 150:1 and 1:1, such as between 100:1 and 4:1, preferably between 50:1 and 8:1, more preferably between 30:1 and 13:1.

4. The composition of any one of the preceding items, wherein the molar ratio of A) to D) is between 150:1 and 3:1, preferably between 90:1 and 10:1, more preferably between 50:1 and 20:1.

5. The composition of any one of the preceding items, wherein A) is serine, preferably L-serine.

6. The composition of any one of the preceding items, wherein B) is N-acetyl cysteine.

7. The composition of any one of the preceding items, wherein C) is carnitine.

8. The composition of any one of the preceding items, wherein D) is nicotinamide riboside.

9. The composition of any one of the preceding items, which is an aqueous solution or suspension.

10. An aqueous solution or suspension comprising:
A) serine;
B) N-acetyl cysteine;
C) carnitine; and
D) nicotinamide riboside, wherein
the molar ratio of A) to B) is between 12:1 and 1:1.5, preferably between and 3:1,
the molar ratio of A) to C) is between 100:1 and 4:1, preferably between 50:1 and 8:1, more preferably between 30:1 and 13:1 and
the molar ratio of A) to D) is between 150:1 and 3:1, preferably between 90:1 and 10:1, more preferably between 50:1 and 20:1.

11. An aqueous solution or suspension comprising:
A) serine;
B) optionally N-acetyl cysteine and/or cysteine;
C) optionally carnitine; and
D) nicotinamide riboside, wherein
the molar ratio of A) to D) is between 90:1 and 10:1 preferably between 50:1 and 20:1, more preferably between 45:1 and 25:1.

12. The solution or suspension of any one of items 9-11, wherein the concentration of A) is 0.20-2.4 mmol/ml, preferably 0.40-2.4 mmol/ml, more preferably 0.60-2.4 mmol/ml.

13. The solution or suspension of any one of items 9-12, wherein the concentration of D) is 0.006-0.12 mmol/ml, preferably 0.012-0.08 mmol/ml, more preferably 0.018-0.07 mmol/ml.

14. The solution or suspension of any one of items 9-13, wherein the concentration of B) is 0.09-0.90 mmol/ml, such as 0.09-0.54 mmol/ml, preferably 0.11-0.40 mmol/ml, more preferably 0.013-0.30 mmol/ml.

15. The solution or suspension of any one of items 9-14, wherein the concentration of C) is 0.009-0.38 mmol/ml, such as 0.009-0.19 mmol/ml, preferably 0.016-0.16 mmol/ml, more preferably 0.028-0.12 mmol/ml.

16. A package, such as a bottle, comprising the solution or suspension of any one of items 9-15.

17. The package of item 16, wherein the volume of the package is 25-1000 ml, such as 50-500 ml.

18. The composition, solution or suspension according to any one of the preceding items for use in a therapeutic method of treatment of a subject.

19. The composition, solution or suspension according to item 18, wherein said therapeutic method is a method of treatment of a medical condition selected from the group consisting of non-alcoholic fatty liver disease (NAFLD), alcoholic fatty liver disease (AFLD), type 2 diabetes, obesity, insulin resistance and dyslipidemia.

20. The composition, solution or suspension according to item 18 or 19, wherein said therapeutic method comprises oral administration of said substances.

21. The composition, solution or suspension according to item 20, wherein said therapeutic method comprises oral administration of:
A) in a dose of 0.48-24 mmol/kg/day, such as 0.48-4.8 mmol/kg/day, such as 1.8-4.8 mmol/kg/day, such as 2.9-4.6 mmol/kg/day;
optionally B) in a dose of 0.31-3.05 mmol/kg/day, such as 0.31-1.84 mmol/kg/day, such as 0.43-1.23 mmol/kg/day;
optionally C) in a dose of 0.031-1.24 mmol/kg/day, such as 0.031-0.620 mmol/kg/day, such as 0.062-0.50 mmol/kg/day, such as 0.093-0.37 mmol/kg/day; and
D) in a dose of 0.020-0.39 mmol/kg/day, such as 0.039-0.31 mmol/kg/day, such as 0.059-0.24 mmol/kg/day.

22. Method of treatment of a medical condition selected from the group consisting of non-alcoholic fatty liver disease (NAFLD), alcoholic fatty liver disease, type 2 diabetes or obesity, comprising oral administration to a subject in need thereof:
A) serine, glycine, betaine, N-acetylglycine, N-acetylserine, dimethylglycine, sarcosine and/or phosphoserine in a dose of 0.48-24 mmol/kg/day, such as 0.48-4.8 mmol/kg/day, such as 1.8-4.8 mmol/kg/day, such as 2.9-4.6 mmol/kg/day;
B) optionally N-acetyl cysteine, cysteine and/or cystine in a dose of 0.31-3.05 mmol/kg/day, such as 0.31-1.84 mmol/kg/day, such as 0.43-1.23 mmol/kg/day;
C) optionally carnitine, deoxycarnitine, gamma-butyrobetaine, 4-trimethylammoniobutanal, 3-hydroxy-N6,N6,N6-trimethyl-L-lysine, N6,N6,N6-trimethyl-L-lysine and/or lysine in a dose of 0.031-1.24 mmol/kg/day, such as 0.031-0.620 mmol/kg/day, such as 0.062-0.50 mmol/kg/day, such as 0.093-0.37 mmol/kg/day;
D) nicotinamide riboside, quinolinate, deamino-NAD+, nicotinate D-ribonucleotide, nicotinamide D-ribonucleotide, nicotinate D-ribonucleoside, nicotinamide and/or nicotinate in a dose of 0.020-0.39 mmol/kg/day, such as 0.039-0.31 mmol/kg/day, such as 0.059-0.24 mmol/kg/day.

23. Method according to item 22, wherein the medical condition is non-alcoholic steatohepatitis (NASH).

24. Method according to item 22 or 23, wherein the treatment is carried out for a period of 1-12 weeks, such as 2-8 weeks.

25. Substances comprising
A) serine, glycine, betaine, N-acetylglycine, N-acetylserine, dimethylglycine, sarcosine and/or phosphoserine,
B) optionally N-acetyl cysteine, cysteine and/or cystine,
C) optionally carnitine, deoxycarnitine, gamma-butyrobetaine, trimethylammoniobutanal, 3-hydroxy-N6,N6,N6-trimethyl-L-lysine, N6,N6,N6-trimethyl-L-lysine and/or lysine and
D) nicotinamide riboside, quinolinate, deamino-NAD+, nicotinate D-ribonucleotide, nicotinamide D-ribonucleotide, nicotinate D-ribonucleoside, nicotinamide and/or nicotinate
for simultaneous, separate or sequential use in a therapeutic method of treatment of a subject.

26. Substances according to item 25, wherein
A) is serine,
B) is N-acetyl cysteine,
C) is carnitine, and
D) is nicotinamide riboside.

27. Substances according to item 26, wherein said therapeutic method is a method of treatment of a medical condition selected from the group consisting of non-alcoholic fatty liver disease (NAFLD), alcoholic fatty liver disease, type 2 diabetes, obesity, insulin resistance and dyslipidemia.

28. Substances according to any one of items 25-27, wherein said therapeutic method comprises oral administration of said substances.

29. Substances according to item 28, wherein said therapeutic method comprises oral administration of:
   A) in a dose of 0.48-24 mmol/kg/day, such as 0.48-4.8 mmol/kg/day, such as 1.8-4.8 mmol/kg/day, such as 2.9-4.6 mmol/kg/day;
   optionally B) in a dose of 0.31-3.05 mmol/kg/day, such as 0.31-1.84 mmol/kg/day, such as 0.43-1.23 mmol/kg/day;
   optionally C) in a dose of 0.031-1.24 mmol/kg/day, such as 0.031-0.620 mmol/kg/day, such as 0.062-0.50 mmol/kg/day, such as 0.093-0.37 mmol/kg/day; and
   D) in a dose of 0.020-0.39 mmol/kg/day, such as 0.039-0.31 mmol/kg/clay, such as 0.059-0.24 mmol/kg/day.

BRIEF DESCRIPTION OF THE FIGURES

FIG. 5A: Hepatic lipids including A) triglycerides, B) cholesterol esters, C) ceramides, D) sphingomyelin, E) phosphatidylethanolamine (normalized to phosphatidylcholine) are shown in mice fed a Western diet (n=10) and supplemented with cocktail (n=10). F) Quantification of serum amino acids from the liver of same mice before and after supplementation. FIG. 5B: G) Analysis of the molecular species of triglycerides extracted from the livers of the mice, Results from the control group (non-treated) are expressed as 100% and results from the treated group are expressed as 96 of the control group. FIG. 5C: The human plasma H) alanine aminotransferase (ALT), I) aspartate aminotransferase (AST), J) alkaline phosphatase (ALP) and K) triglycerides (TGs) levels are presented in each human subject involved in the study before and after the supplementation with serine, Each study subject received one oral dose of L-serine (200 mg/kg) per day for 14 days.

DETAILED DESCRIPTION

Figure 6:
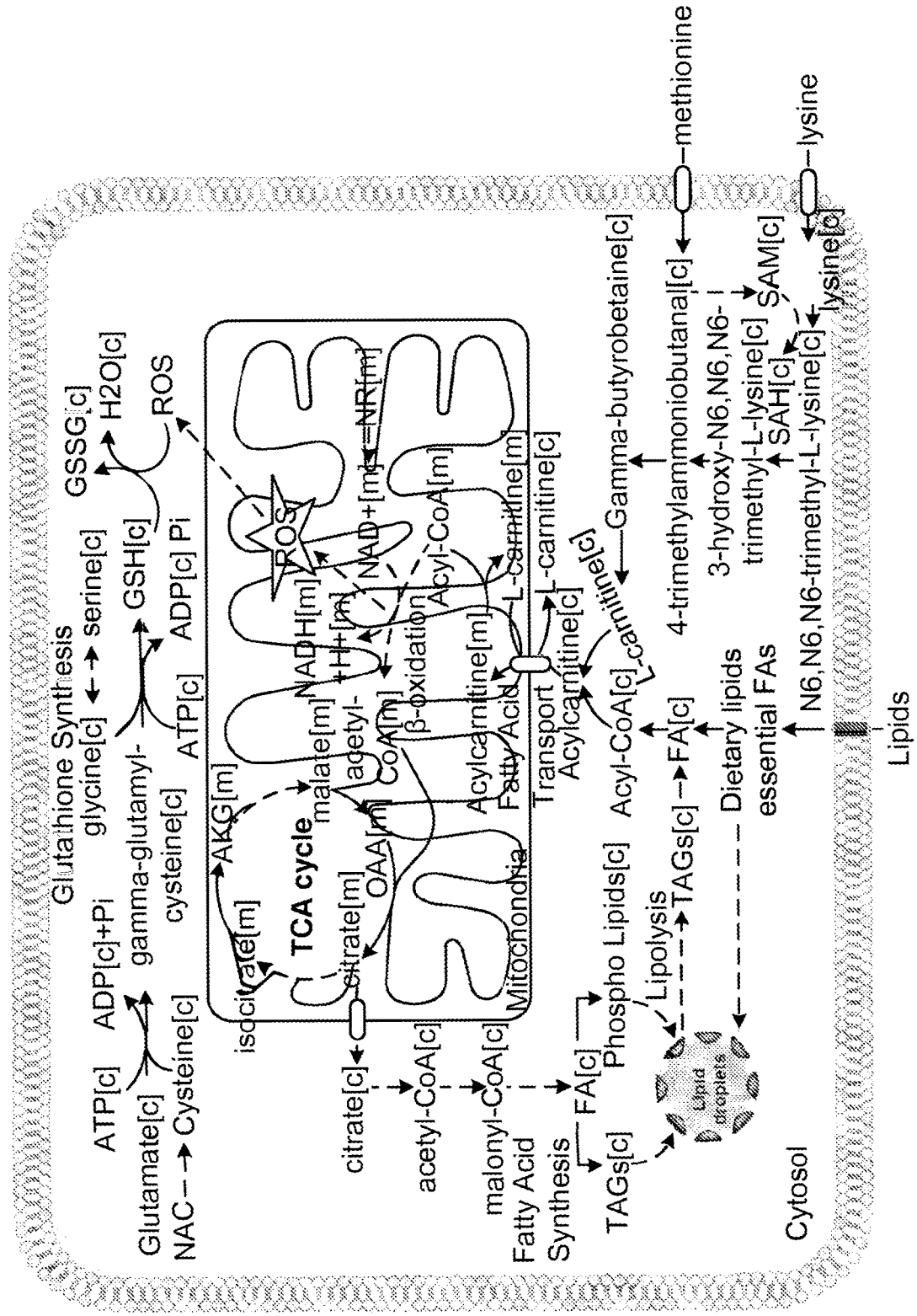
FIG. 6 shows a model of the biochemical pathways related to β-oxidation of fatty acids in liver cells, which highlights the impact of supplementation of serine, NAC, NR and L-carnitine.

Through personalized modelling of the subjects with HS, the inventors have observed that liver has a capacity to clear accumulated fatty acids by oxidizing them in the liver. A strategy of up to three steps has been developed: i) increasing the uptake of fatty acids into the mitochondria, ii) increasing the oxidation of the fatty acids in the mitochondria and iii) increasing the availability of GSH (FIG. 6). A cocktail or combination of molecular products can be supplemented to boost two or more of these metabolic processes and eventually decrease the amount of fatty acids in the liver. L-carnitine and NR can be included into the cocktail or combination to increase the transfer of fatty acids from cytosol to mitochondria and to boost the level of NAD+ which is required for fatty acid oxidation in mitochondria, respectively. Decreased electron transport chain function combined with increased rates of fatty acid oxidation may lead to the accumulation of products of incomplete fatty acids oxidation, which combined with increased levels of reactive oxygen species, may contribute to insulin resistance. To avoid these, the level of GSH can be increased by including serine and NAC into the content of the cocktail or combination.

As a first aspect of the present disclosure, there is provided a composition comprising:
   A) serine, glycine, betaine, N-acetylglycine, N-acetylserine, dimethylglycine, sarcosine and/or phosphoserine;
   B) optionally N-acetyl cysteine, cysteine and/or cystine;
   C) optionally carnitine, deoxycarnitine, gamma-butyrobetaine, 4-trimethylammoniobutanal, 3-hydroxy-N6, N6,N6-trimethyl-L-lysine, N6,N6,N6-trimethyl-L-lysine and/or lysine; and
   D) nicotinamide riboside, quinolinate, deamino-NAD+, nicotinate D-ribonucleotide, nicotinamide D-ribonucleotide, nicotinate D-ribonucleoside, nicotinamide and/or nicotinate.

In one embodiment of the first aspect, the composition comprises A), B), C) and optionally D).

In group A), serine and glycine are preferred. The most preferred substance in group A) is serine, which is usually provided as L-serine. As shown in the experimental section below, the effect of serine that was predicted by the model has been confirmed in a human study and an animal study.

In group B), N-acetyl cysteine (NAC) and cysteine are preferred. The most preferred substance in group B) is NAC. As shown in the experimental section below, the effect of NAC that was predicted by the model has been confirmed in an animal study.

The substance of group C) is preferably carnitine, optionally in the form of a carnitine salt, such as carnitine tartrate. Most preferably, the substance of group C) is L-carnitine, optionally in the form of a L-carnitine salt, such as L carnitine tartrate. The inventors' model shows that there is a need for increased uptake of fatty acids in subjects with high ITS (data not shown). Carnitine can be supplemented to achieve such increased uptake.

The substance of group D) is preferably nicotinamide riboside (NR). As shown in the experimental section below, the effect of NR that was predicted by the model has been confirmed in an animal study.

The substance(s) of group A) is preferably included in a higher molar amount than the substance(s) of group D). When efficacy and toxicity is also considered (see the discussion about doses below), the molar ratio of A) to D) is normally between 250:1 and 1.5:1 and typically between 150:1 and 3:1. Preferably, the molar ration is between 90:1 and 10:1, more preferably between 50:1 and 20:1.

In embodiments including the substance(s) of group B), the molar ratio of A) to B), considering efficacy and toxicity, is typically between 16:1 and 1:4, preferably between 12:1 and 1.5:1 and more preferably between 10:1 and 3:1.

In embodiments including the substance(s) of group C), the molar ratio of A) to C), considering efficacy and toxicity, is normally between 150:1 and 1:1, typically between 100:1 and 4:1 preferably between 50:1 and 8:1 and more preferably between 30:1 and 13:1.

The above ratios entails that a patient consuming the composition can obtain appropriate doses of the respective substances.

In one embodiment, the composition of the first aspect is a solid, such as a solid powder. Such a powder can be mixed with water, e.g., by the patient/consumer, a nurse or a physician. However, the composition of the first aspect is preferably and an aqueous solution or suspension ("cocktail"), which facilitates convenient oral administration. Such an aqueous solution or suspension is preferably ready to drink.

As a particularly preferred embodiment of the first aspect, there is provided an aqueous solution or suspension comprising:
A) serine;
B) N-acetyl cysteine;
C) carnitine; and
D) nicotinamide riboside, wherein
the molar ratio of A) to B) is between 12:1 and 1:1.5, preferably between 10:1 and 3:1,
the molar ratio of A) to C) is between 100:1 and 4:1, preferably between 50:1 and 8:1, more preferably between 30:1 and 13:1 and
the molar ratio of A) to D) is between 150:1 and 3:1, preferably between 90:1 and 10:1, more preferably between 50:1 and 20:1.

As another particularly preferred embodiment of the first aspect, there is provided an aqueous solution or suspension comprising:
A) serine;
B) optionally N-acetyl cysteine and/or cysteine;
C) optionally carnitine; and
D) nicotinamide riboside, wherein
the molar ratio of A) to D) is between 90:1 and 10:1, preferably between 50:1 and 20:1, more preferably between 45:1 and 25:1.

In embodiments of the solution or suspension according to the first aspect:
the concentration of A) is typically 0.20-2.4 mmol/mi, preferably 0.40-2.4 mmol/ml and more preferably 0.60-2.4 mmol/ml; and/or
the concentration of D) is typically 0.006-0.12 mmol/ml, preferably 0.012-0.08 mmol/ml and more preferably 0.018-0.07 mmol/ml.

When included in the solution or suspension according to the first aspect:

the concentration of B) is normally 0.09-0.90 mmol/ml, typically 0.09-0.54 mmol/ml preferably 0.11-0.40 mmol/ml and more preferably 0.013-0.30 mmol/ml; and/or
the concentration of C) is normally 0.009-0.38 mmol/ml, typically 0.009-0.19 mmol/ml, preferably 0.016-0.16 mmol/ml and more preferably 0.028-0.12 mmol/ml.

The solution or suspension of the first aspect may be provided in a package for convenient handling and distribution. Further, the volume of such a package may be such that drinking the whole contents of the package at once or during a single day results in oral administration of appropriate doses of the substances in the solution or suspension. In one embodiment, the volume of the package is 25-1000 ml. The volume is preferably 50-500 ml. When it is intended that the consumer/patient shall drink more than one package per day, the volume is typically relatively low, such as 25-500 ml, preferably 25-400 ml.

In one embodiment, the packaged solution or suspension comprises 48-478 mmol of A). Thereby, the dose of A) is effective, but not toxic. In a preferred embodiment, A) is serine in an amount of 5-50 g, more preferably 10-50 g.

In an alternative of complimentary embodiment, the packaged solution or suspension comprises 2.0-39.2 mmol of D) when D) is NR and 2.0-196 mmol of D) when D) is not NR. Thereby, the dose of D) is effective, but not toxic. In a preferred embodiment, D) is NR in an amount of 0.5-10 g, more preferably 1.5-6 g.

When the composition of the first aspect is a powder, it may also be packaged. It follows from the discussion above that such a pack of powder may comprise 48-478 mmol of A) and/or 2.0-39.2 mmol of D) when D) is NR and 2.0-196 mmol of D) when D) is not NR. Further, such as packed powder preferably comprises serine in an amount of 5-50 g and/or NR in an amount of 0.5-10 g. More preferably, such a packed powder comprises serine in an amount of 10-50 g and/or NR in an amount of 1.5-6.0 g.

The substances of the present disclosure are preferably a significant part of the composition, solution or suspension of the first aspect. For example, the substances included in groups A)-D) may amount to at least 10%, such as at least 25%, such as at least 50% of the dry weight of the composition, solution or suspension of the first aspect. In one embodiment, the weight of serine is at least 10%, such as at least 25%, such as at least 40% of the dry weight of the composition, solution or suspension of the first aspect.

The composition of the first aspect may comprise one or more tasting agent(s), such as one or more sweetener(s) (e.g., sucralose) and/or one or more flavor agent(s). It may also comprise a lubricant, such as a polyethylene glycol lubricant (e.g., Polyglycol 8000 PF (Clariant)).

It follows from the discussion above that the composition may be used for therapeutic purposes. As a second aspect of the present disclosure, there is thus provided a composition, solution or suspension according to the first aspect for use in a therapeutic method of treatment of a subject.

The therapeutic method may be a method of treatment of a medical condition selected from the group consisting of non-alcoholic fatty liver disease (NAFLD), alcoholic fatty liver disease (AFLD), type 2 diabetes, obesity, insulin resistance and dyslipidemia.

In a preferred embodiment, the therapeutic method is a method of treatment of a medical condition selected from the group consisting of NAFLD and AFLD. In a particularly preferred embodiment, the therapeutic method is a method of treatment non-alcoholic steatohepatitis (NASH), which is part of the group of conditions called NAFLD, NASH is normally considered to be the most extreme form of NAFLD and is often regarded as a major cause of cirrhosis of the liver.

In an embodiment of the second aspect, the therapeutic method comprises oral administration of said composition, solution or suspension.

To achieve a therapeutic effect without reaching toxic levels in the human body, the inventors have found the following doses for the substances of the present disclosure:
A) Represented by serine
  Daily dose range: 50-2000 mg/kg (0.478-24 mmol/kg), a single dose shall however preferably not exceed 500 mg/kg (4.78 mmol/kg)
  Suggested dose: 400 mg/kg/day (3.8 mmol/kg/day)
B) Represented by N-acetyl cysteine (NAC)
  Daily dose range: 50-500 mg/kg (0.306-3.06 mmol/kg)
  Suggested dose: 100 mg/kg/day (0.613 mmol/kg/day)
C) Represented by L-carnitine
  Daily dose range: 5-200 mg/kg (0.031-1.24 mmol/kg)
  Suggested dose: 30 mg/kg/day (0.186 mmol/kg/day)
D) Represented by nicotinamide riboside (NR)
  Daily dose range: 5-100 mg/kg (0.0196-0.392 mmol/kg)*
  Suggested dose: 30 mg/kg/day (0.118 mmol/kg/day)
  *When D) is not NR, the daily dose range is 0.0196-1.96 mmol/kg.

Accordingly, the therapeutic method of the second aspect may for example comprise oral administration of:
A) in a dose of 0.48-24 mmol/kg/day, typically 0.48-4.8 mmol/kg/day, preferably 1.8-4.8 mmol/kg/day and more preferably 2.9-4.6 mmol/kg/day; optionally B) in a dose of 0.31-3.05 mmol/kg/day, preferably 0.31-1.84 mmol/kg/day and more preferably 0.43-1.23 mmol/kg/day; optionally C) in a dose of 0.031-1.24 mmol/kg/day, typically 0.031-0.620 mmol/kg/day, preferably 0.062-0.50 mmol/kg/day and more preferably 0.093-0.37 mmol/kg/day; and/or
D) in a dose of 0.0196-1.96 mmol/kg/day, typically 0.020-0.39 mmol/kg/day, preferably 0.039-0.31 mmol/kg/day and more preferably 0.059-0.24 mmol/kg/day, provided that the dose is not higher than 0.39 mmol/kg/day when D) is NR.

The daily dose may be reached by administrating one or more doses per day to the consumer/patient. For example, the patient may have one, two or three drinks of the above-mentioned solution or suspension per day. Each dose or drink preferably comprises no more than 4.78 mmol/kg of A).

The therapeutic method of the second aspect may be carried out for a period of 1-12 weeks, such as 2-8 weeks, preferably 3-8 weeks. If the treatment is carried out for a longer period, the risk of side effects increases. A shorter period may not be sufficient for a therapeutic effect.

As a third aspect of the present disclosure, there is provided a method of treatment of a medical condition selected from the group consisting of non-alcoholic fatty liver disease (NAFLD), alcoholic fatty liver disease, type 2 diabetes or obesity, comprising oral administration to a subject in need thereof:
A) serine, glycine, betaine, N-acetylglycine, N-acetylserine, dimethylglycine, sarcosine and/or phosphoserine in a dose of 0.48-24 mmol/kg/day, such as 0.48-4.8 mmol/kg/day, such as 1.8-4.8 mmol/kg/day such as 2.9-4.6 mmol/kg/day;
B) optionally N-acetyl cysteine, cysteine and/or cystine in a dose of 0.31-3.05 mmol/kg/day, such as 0.31-1.84 mmol/kg/day, such as 0.43-1.23 mmol/kg/day;
C) optionally carnitine, deoxycarnitine, gamma-butyrobetaine, 4-trimethylammoniobutanal, 3-hydroxy-N6, N6,N6-trimethyl-L-lysine, N6,N6,N6-trimethyl-L-lysine and/or lysine in a dose of 0.031-1.24 mmol/kg/day, such as 0.031-0.620 mmol/kg/day, such as 0.062-0.50 mmol/kg/day, such as 0.093-0.37 mmol/kg/day;
D) nicotinamide riboside (NR), quinolinate, deamino-NAD+, nicotinate D-ribonucleotide, nicotinamide D-ribonucleotide, nicotinate D-ribonucleoside, nicotinamide and/or nicotinate in a dose of 0.0196-1.96 mmol/kg/day, such as 0.020-0.39 mmol/kg/day, such as 0.039-0.31 mmol/kg/day, such as 0.059-0.24 mmol/kg/day, provided that the dose is not higher than 0.39 mmol/kg/day when D) is NR.

The embodiments and examples of the first and second aspect apply to the third aspect *mutatis mutandis*.

For the patient/consumer, it is not necessary to take the substances of the present disclosure simultaneously. A therapeutic effect can also be achieved if the substances are taken separately or sequentially, preferably within a day and more preferably within an hour.

As a fourth aspect of the present disclosure, there is thus provided substances comprising:
A) swine, glycine, betaine, N-acetylglycine, N-acetylserine, dimethylglycine, sarcosine and/or phosphoserine;
B) optionally N-acetyl cysteine, cysteine and/or cysteine;
C) optionally carnitine, deoxycarnitine, gamma-butyrobetaine, trimethylammoniobutanal, 3-hydroxy-N6,N6, N6-trimethyl-L-lysine, N6,N6,N6-trimethyl-L-lysine and/or lysine; and
D) nicotinamide riboside, quinolinate, deamino-NAD+, nicotinate D-ribonucleotide, nicotinamide D-ribonucleotide, nicotinate D-ribonucleoside, nicotinamide and/or nicotinate for simultaneous, separate or sequential use in a therapeutic method of treatment of a subject.

The fourth aspect may for example be a combined preparation of two or more units, such as a first unit comprising A), a second unit comprising D), optionally a third unit comprising B) and optionally a fourth unit comprising C).

The embodiments and examples of the first and second aspect apply to the third fourth *mutatis mutandis*.

EXPERIMENTS

Experimental Procedures

Subjects 86 subjects with varying degrees of HIS were recruited for studying the response of liver to the HS. The clinical characteristics of the subjects are presented in Table 1. Also, liver tissue samples from 12 morbidly obese subjects that underwent bariatric surgery were collected. The characteristics of the morbidly obese subjects are presented in Table 2. The mRNA expression of the identified target genes was measured in liver of obese and healthy subjects. In order to show the effect of the serine on the liver, another six subjects were recruited and the subjects' characteristics before and after serine supplementation are presented in Table 3. Subjects included in the studies met all the criteria for NAFLD including exclusion of other chronic liver diseases such as viral hepatitis, risky alcohol consumption, metabolic disorders (e.g., hemochromatosis).

TABLE 1

Clinical characteristics of the 86 study participants. Data are presented as means ± SD. P-value indicates significance level of difference between the subjects with low and high hepatic steatosis (HS).

| Characteristic | Low HS HS (%) < 5.5 n = 43 | High HS HS (%) > 5.5 n = 43 | P-value |
|---|---|---|---|
| Liver fat (%) | 2.8 ± 1.7 | 13.4 ± 6.4 | <0.05 |
| Age (years) | 52.1 ± 8.4 | 52.6 ± 8.0 | 0.76 |
| Weight (kg) | 92.4 ± 11.2 | 102.2 ± 14.0 | <0.05 |
| Body Mass Index (BMI) (kg/m$^2$) | 29.7 ± 3.2 | 32.9 ± 3.4 | <0.05 |
| Fasting plasma glucose (mmol/L) | 5.5 ± 0.5 | 5.85 ± 0.6 | <0.05 |
| Fasting plasma insulin (FPI) (mU/L) | 7.6 ± 5.0 | 14.0 ± 7.0 | <0.05 |
| HOMA-IR | 1.9 ± 1.3 | 3.7 ± 2.0 | <0.05 |
| C-reactive protein (CRP) (mg/L) | 2.4 ± 2.8 | 3.3 ± 3.3 | 0.31 |
| Plasma triglycerides (TG) (mmol/L) | 1.7 ± 0.6 | 2.1 ± 0.8 | <0.05 |
| Apolipoprotein B (apoB) (mg/dl) | 90.2 ± 29.0 | 97.4 ± 30.7 | 0.30 |
| Total cholesterol (mmol/L) | 4.9 ± 0.85 | 5.1 ± 0.7 | 0.31 |
| HDL cholesterol (mmol/L) | 1.1 ± 0.3 | 1.1 ± 0.3 | 0.96 |
| Alanine aminotransferase (ALT) (U/L) | 23.5 ± 9.3 | 38.9 ± 28.3 | <0.05 |
| Aspartate aminotransferase (AST) (U/L) | 21.9 ± 5.1 | 23.2 ± 5.8 | 0.41 |
| Alkaline phosphatase (ALP) (U/L) | 63.2 ± 16.7 | 70.5 ± 19.3 | 0.16 |
| γ-Glutamyl transferase (μGT) (U/L) | 27.6 ± 16.4 | 31.2 ± 13.9 | 0.40 |

TABLE 2

Clinical characteristics of the twelve obese subjects underwent bariatric surgery with high HS. Data are presented as means ± SD.

| Clinical variable | Obese subjects with high HS (n = 12) |
|---|---|
| Age (years) | 39.3 ± 10.9 |
| Weight (kg) | 122.9 ± 12.8 |
| Body Mass Index (BMI) (kg/m$^2$) | 43.6 ± 3.6 |
| Fasting plasma glucose (mmol/L) | 5.6 ± 0.6 |
| Fasting plasma insulin (FPI) (pmol/L) | 128.7 ± 49.9 |
| HOMA-IR | 4.7 ± 1.9 |
| Plasma triglycerides (TG) (mmol/L) | 1.5 ± 0.5 |
| Total cholesterol (mmol/L) | 5.1 ± 0.7 |
| LDL cholesterol (mmol/L) | 3.1 ± 0.7 |
| HDL cholesterol (mmol/L) | 1.3 ± 0.3 |
| Alanine aminotransferase (ALT) (U/L) | 25.3 ± 16.3 |
| γ-Glutamyl transferase (μGT) (U/L) | 30.7 ± 23.2 |

TABLE 3

Clinical characteristics of the six subjects involved in serine supplementation study. Data are presented as means ± SD. P-value indicates the significance-level of difference before and after the oral supplementation of serine.

| Clinical variable | Baseline n = 6 | After serine n = 6 | P-value |
|---|---|---|---|
| Liver fat (%) | 26.8 ± 6.0 | 20.4 ± 7.0 | <0.05 |
| Age (years) | 56.7 ± 5.2 | 56.7 ± 5.2 | — |
| Weight (kg) | 103.0 ± 14.3 | 103.0 ± 13.9 | — |
| Body Mass Index (BMI) (kg/m$^2$) | 32.5 ± 2.70 | 32.5 ± 2.60 | — |
| Alanine aminotransferase (ALT) (U/L) | 50.8 ± 15.2 | 37.6 ± 5.3 | <0.05 |
| Aspartate aminotransferase (AST) (U/L) | 34.5 ± 8.10 | 27.4 ± 8.4 | <0.05 |
| Alkaline phosphatase (ALP) (U/L) | 76.3 ± 17.2 | 71.3 ± 17.9 | <0.05 |
| γ-Glutamyl transferase (μGT) (U/L) | 63.8 ± 12.9 | 62.3 ± 16.3 | 0.30 |
| Fasting plasma glucose (mmol/L) | 6.57 ± 1.41 | 6.33 ± 1.41 | 0.25 |
| Fasting plasma insulin (FPI) (pmol/L) | 46.3 ± 33.8 | 34.7 ± 25.2 | 0.23 |
| HOMA-IR | 2.15 ± 1.85 | 1.54 ± 1.49 | 0.18 |
| LDL cholesterol (mmol/L) | 3.68 ± 0.80 | 3.85 ± 0.94 | 0.50 |
| HDL cholesterol (mmol/L) | 1.00 ± 0.21 | 1.02 ± 0.18 | 0.30 |
| Plasma triglycerides (TG) (mmol/L) | 6.90 ± 6.65 | 3.63 ± 1.81 | 0.13 |
| Total cholesterol (mmol/L) | 6.23 ± 1.49 | 5.85 ± 1.15 | 0.18 |
| Bilirubin (μmol/L) | 7.33 ± 4.11 | 6.48 ± 3.94 | 0.13 |

Determination of Liver, Subcutaneous and Intra-Abdominal Fat

Magnetic resonance experiments were performed using three 1.5 T clinical imagers (1× Sonata and 2× Avanto, Siemens, Erlangen, Germany). Liver fat content was determined using proton magnetic resonance spectroscopy and subcutaneous abdominal and visceral fat was measured by magnetic resonance imaging (Adiels et al, 2006; Lundbom et al, 2011).

Measurement of Flux Data

Lipoprotein fluxes were measured in 73 of the fasted subjects using stable isotope infusion. After a bolus infusion of d3-leucine and d5-glycerol, large (VLDL1) and small (VLDL2) VLDL subfractions were isolated by ultracentrifugation and the enrichment of free leucine in plasma, leucine in apoB and glycerol in TG was measured using gas chromatography-mass spectrometry (Adiels et al, 2005). Metabolic fluxes were calculated using mathematical modelling as previously described (Adiels et al, 2005).

Muscle Mass and Fat Mass Calculations

The muscle mass of each subject was calculated from lean mass using the previously described relationship (Clark et al, 2014) based on their fat mass.

A linear equation was fitted between BMI and fat mass of 44 of the subjects to predict the missing fat mass in the remaining 29 subjects. The linear equation was defined as: fat mass (kg)=1.763*BMI−26.75 ($R^2$=0.69). Using this equation, fat mass was calculated for the 29 subjects and the lean mass was then calculated by subtracting the fat mass from the body weight of the subjects. Finally, the muscle mass for each subject was calculated based on the previously derived equation (Clark et al, 2014): muscle mass=0.63*lean mass−4.1.

Inputs and Outputs for the Liver GEM in the Fasting State

During fasting conditions, the liver takes up gluconeogenic substrates, non-esterified FAs and AAs and produces blood glucose (as an energy substrate for the brain), VLDL (as an energy substrate for the rest of the body), ketone bodies and plasma proteins. The proteins secreted by the liver (mainly albumin) are not necessarily a net loss for the liver since protein can be recycled. However, in this study, the urea loss from urine was used as a proxy for the net loss of protein from the liver.

The input variables in the model are thus: i) AAs, ii) lactate and iii) FAs and glycerol. The output variables are: iv) glucose derived from gluconeogenesis and glycogenolysis, v) ketone bodies as well as the measured VLDL secretion.

i) AAs:

In the fasting state, some AAs are released by muscle tissue. Pozefsky et al (Pozefsky et al, 1976) experimentally quantified the AA release from muscle tissue in the fasting state. They found that around 60% of all the AAs released from muscle are glutamine and alanine, which are the main substrates, used for gluconeogenesis in the liver. These experimentally measured values were incorporated into the model based on the muscle mass of each subject.

Adipose tissue also releases AAs into the blood. Since the subjects in the present study had varying degrees of adiposity, it is important to know if the release of AA differs between lean and obese subjects. Patterson et al (Patterson et al, 2002) found that although AA release is proportional to the amount of fat tissue a person has, it also depends on blood flow, which decreases as the amount of fat tissue increases. Thus, the release of AAs from adipose tissue is independent of obesity. Therefore, an additional input of AAs based on adipose tissue mass was included in the model. This contribution was calculated based on the study of Frayn and Karpe (Frayn & Karpe, 2014) where they measured how much blood flows in and out of adipose tissue (3-4 ml/min, 100 g fat tissue).

Another method (Ardilouze et al, 2004) provided information on a person's fat mass based on their PMI, gender and age according to the formula: body fat percent= (1.2*BMI)+(0.23*age)−(10.8*gender)−5.4, where gender is for female and 1 for male (Deurenberg et al, 1991). This resulted in an average body fat mass of around 15 kg which gave an average blood flow of the whole adipose tissue of around 31.5 L/h. Since Patterson et al (Patterson et al, 2002) provided the values for the release of AAs based on body fat (in µmol/L), the release of AAs by the adipose tissue (in mmol/h) was calculated for each subject and used as an input to the personalized models.

Muscle tissue and adipose tissue are not the only sources of AAs for the liver during starvation. It has been shown that rat liver catabolizes around 25% of all intracellular proteins during the first 24 h of starvation (Cuervo & Dice, 1996). In the present analysis, the total AAs released from muscle and adipose tissues do not seem to satisfy the liver demand for AAs. During 16 h of fasting, the urea excretion rate measured in humans was 392±44 mmol urea/24 h (Norrelund et al, 2001). Assuming an average nitrogen content of 1.45 nitrogen atoms per AA and an average AA molar mass of 136.5 g/mol, the consumption of AAs in the liver after a 16 h fast thus averaged close to 80 g/day (392 mmol/24 h*136.5 g/mol/1000/1.45=77.6 g AAs/day). This value was almost constant after 40 h of fasting (440 mmol/24 h), indicating maintained (or even increased) AA consumption in the fasting liver. The total amount of AAs released by muscle and adipose tissues was calculated to be close to 35 g/day indicating that the liver, in the present study, likely catabolites itself in relatively large quantities—approximately 40-45 g/day. The AA composition of human liver has been measured by Benga & Ferdinand (Benga & Ferdinand, 1995). The molar ratios of the AAs in liver were incorporated into an additional input reaction to the model in order to achieve realistic AA net consumption values.

ii) Lactate

Lactate is used as a gluconeogenic substrate in the liver. Wallace (Wallace, 2002) claimed that the total amount of lactate produced by red blood cells, the kidney, the medulla and the retina is around 40 g per day assuming resting conditions. In addition, an extra 40 g is produced by the rest of the body thus totaling around 80 g. This corresponds to around 3.3 g/h=37 mmol/h and was used as an input to the model.

iii) FAs and Glycerol

FAs are used by the liver for production of TG in VLDL. Glycerol is a by-product of TG breakdown and subsequent FA release by adipose tissue and can be used as a gluconeogenic substrate. The FA and glycerol release from adipose tissue was estimated based on a study by McQuaid et al (McQuaid et al, 2011) and values of FA and glycerol release from adipose tissue were retrieved for each subject in the fasting state. This average value was around. 30 µmol/min,kg fat mass which is equal to 1.8 mmol/h,kg fat mass. Since the molar ratio of glycerol release to FA release is 1:3, the glycerol release was set as 0.6 mmol/h,kg fat mass. Both of these values were considered as upper bounds. However, Bickerton et al (Bickerton et al, 2007) measured the total FA influx into muscle in fasting subjects and found that only around 4% of the FA released by adipose tissue was taken up by muscle, Thus, the released FA of 1.8 mmol/h was used as an input to the model.

iv) Gluconeogenesis and Glycogenolysis

Lactate, glutamine, alanine and glycerol are the main gluconeogenic substrates. Another source of glucose is glycogen breakdown. McQuaid et al (McQuaid et al, 2011) and Hellerstein et al (Hellerstein et al, 1997) reported that under normal overnight fasting conditions, the contribution of gluconeogenesis and glycogen breakdown to liver glucose output is roughly equal. McQuaid et al (McQuaid et al, 2011) also found that glycogen breakdown is approximately 5.5 µmol/kg/min in humans after an overnight fast Which corresponds to an average contribution from glycogenolysis of around 5.7 g glucose/h for the subjects in the present study. The brain requires approximately 6 g glucose/h early in fasting when ketone body production is still low (Bourre, 2006). This suggests that during overnight fasting conditions the total glucose output from the liver is in the order of 10-15 g/h and it is definitely higher than 6 g/h. In conclusion, an absolute minimum contribution of gluconeogenesis to glucose output was set as 16.7 mmol/h (3 g/h).

v) Ketone Bodies

The total ketone body production in obese humans increases dramatically up to around 60 mmol/h after 2-3 days of fasting and up to around 75 mmol/h after 17-24 days of fasting (Reichard et al, 1974). However, during an overnight fast, the glycogenolysis should satisfy the majority of the brain's energy demand and the ketone body production rates for acetoacetate and beta-hydroxybutyrate were therefore set at a lower bound of 0.1 mmol/h in the models.

Personalized Genome-Scale Metabolic Models for Liver Tissue

A functional GEM for hepatocytes in liver, iHepatocytes2322, was reconstructed based on hepatocyte-specific proteomics data in Human Protein Atlas (HPA, http://www.proteinatlas.org) (Uhlen et al, 2015). Use of iHepatocytes2322 in conjunction with flux balance analysis allowed for in silico metabolic simulation of liver for each subject involved in the study. The measured/calculated uptake and secretion rate of the key metabolites were incorporated into each GEM and predicted the intracellular liver fluxes of each patient. During the personalized simulation of liver tissue GEMs, the uptake of oxygen, phosphate, minerals, etc. by the model was allowed and the uptake of other metabolites was blocked since the fasting state was simulated. After setting all the bounds, the fluxes of all the subjects were calculated by minimizing the sum of fluxes, based on the assumption that the cells will reduce the pathway usage to a minimum for economic reasons. To test the robustness of the result, the fluxes were also calculated by random sampling without minimizing the flux sum and the same key results were observed.

To investigate the contribution of personalized inputs and outputs (uptake of FAs and VLDL secretion) to the inventors' conclusions, a random control analysis (a random value with the range of the maximum and minimum value of all the patients) was performed. It was found that when using random FA uptake or VLDL secretion alone as an input or output to the personalized models, the correlation between reactions carried by NNT and GSR and HS was significantly decreased. Moreover, when both random FA uptake and VLDL secretion were used, the correlation became non-significant. It was thus concluded that both personalized inputs and outputs are driving the conclusions reached in the study.

Metabolomics Data

Non-targeted metabolite detection and quantification was conducted by the metabolomics provider Metabolon Inc. (Durham, USA) on fasting plasma samples collected from the subjects with varying degrees of HS. Samples were prepared using the automated. MicroLab STAR® system from Hamilton Company. A recovery standard was added before the first step in the extraction process for quality control purposes. To remove protein and dissociated small molecules bound to protein or trapped in the precipitated protein matrix, and to recover chemically diverse metabolites, proteins were precipitated with methanol under vigorous shaking for 2 min (Glen Mills GenoGrinder 2000) followed by centrifugation. The resulting extract was divided into four fractions: one for analysis by UPLC-MS/MS with positive ion mode electrospray ionization, one for analysis by UPLC-MS/MS with negative ion mode electrospray ionization, one for analysis by GC-MS and one sample reserved for backup.

Following log transformation, with the minimum observed value for each compound, Welch's two-sample t-test was used to identify the metabolites that differed significantly between subjects with high and low HS. P-values were corrected for multiple testing. During the identification of the significant metabolites as well as the significantly correlated metabolites, no data were imputed for the missing values. The correlation analysis between the metabolites was performed if both metabolites were detected in at least 30 subjects involving in the study.

Mouse Experiments

Twenty male C57BL/6N mice were fed a standard mouse chow diet (Purina 7012, Harlan Teklad) and housed in a 12-h light-dark cycle. From the age of 8 weeks mice were fed a Western diet (TD.88137, Harlan Laboratories, WI, USA) for 14 days. The mice were then divided into two groups of 10 mice. One group of mice was given the Western diet supplemented with NR (400 mg/kg) and Serine (30 mg/kg) a day la gavage and NAC (1 g/l) in the drinking water for 14 days. The other group was only given the western diet for the 14 days. Ali procedures were approved by the local animal ethics committee and performed in accordance with mandated guidelines.

Lipid Extraction and Analysis

Lipids were extracted as described previously (Lofgren et al, 2012). Internal standards were added during the extraction. Lipids were analyzed using a combination of HPLC and mass spectrometry as described (Stahiman et al, 2013). Briefly, straight phase HPLC was used to purify ceramides (CER). Cholesteryl ester (CE), triacylglycerol (TAG), phosphatidyletanolamine (PE), phosphatidylcholine (PC), sphingomyelin (SM) were quantified using a QTRAP 5500 mass spectrometer (Sciex, Concord, Canada) equipped with a robotic nanoflow ion source, TriVersa NanoMate (Advion BioSciences, Ithaca, NJ), CER were analyzed using reversed phase HPLC coupled to a triple quadrupole Quattro Premier mass spectrometer (Waters, Milford, MA, USA).

Human Study: Supplementation of Serine

The effect of short-term dietary supplementation with serine on HS and fasting levels of Plasma markers of liver functions was assessed in six subjects with high. HS. Characteristics of the six subjects before and after the supplementation are presented in Table 3. Each patient received one oral dose of ~20 g of L-serine (200 mg/kg) per day for 14 days.

RESULTS

Figure 1A:
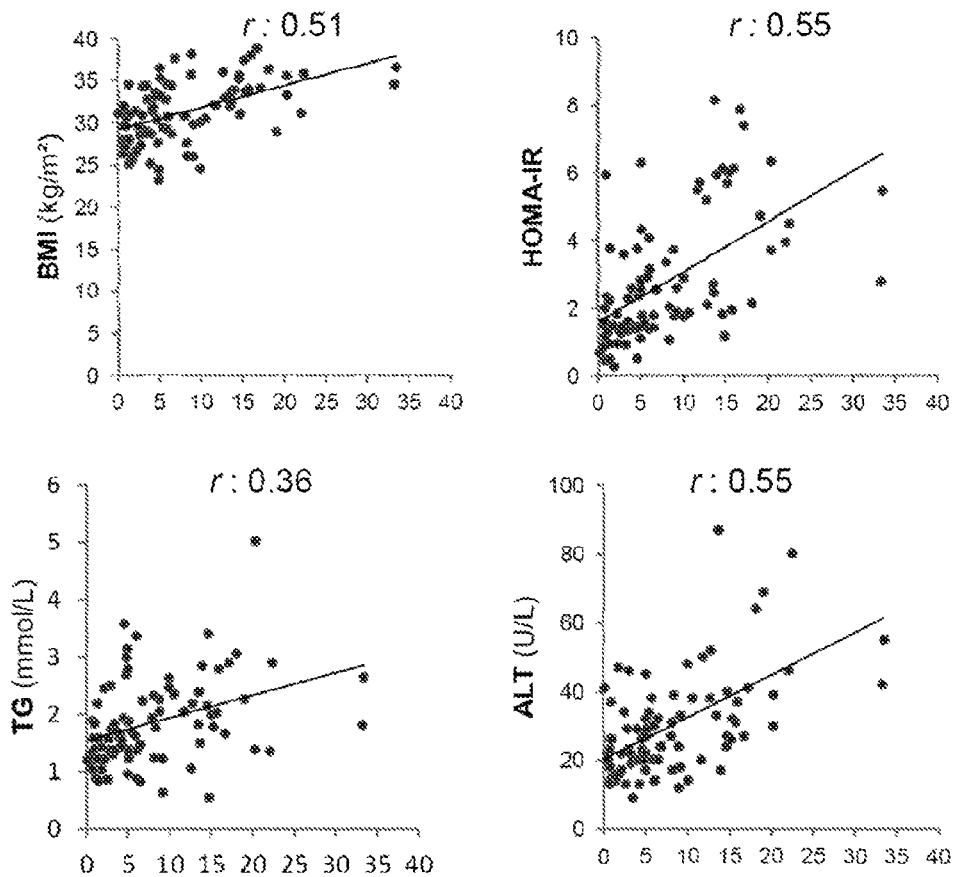
FIGS. 1A-1B: A) Body mass index (BMI), insulin resistance (HOMA-IR), plasma triglycerides (TG) and alanine aminotransferase ALT levels are significantly correlated with the independently measured liver fat. B) The subjects are categorized in to two groups: high HS and low HS. Body mass index (BMI), fasting plasma insulin (FPI), plasma triglycerides (TG) and plasma (ALT) levels are found to be significantly different between two groups. Data are presented as means ±SD.

Characteristics of Subjects with Varying Degrees of HS 86 subjects (75 men and 11 women) were recruited and the liver fat content of each subject was determined using magnetic resonance spectroscopy (Adiels et al, 2006; Lundbom et al, 2011). The Pearson correlation coefficient (r) between HS and other clinical parameters was calculated and it was found that HS was significantly (P-value<0.05) positively correlated with weight, body mass index (BMI), insulin resistance (HOMA-IR), plasma triglyceride (TG) and the liver enzyme alanine aminotransferase (ALT) levels (FIG. 1A). The ratio of ALT to aspartate transaminase (AST) also significantly (P-value<0.05) correlated (r=0.57) with HS. None of the other liver-related clinical parameters (AST, alkaline phosphatase (ALP) and γ-glutamyl transferase (μGT)), blood lipid-related parameters (high-density lipoprotein (HDL) cholesterol, total cholesterol and apolipoprotein B (apoB)) nor the inflammation marker C-reactive protein (CRP) correlated significantly with HS.

Figure 1B:
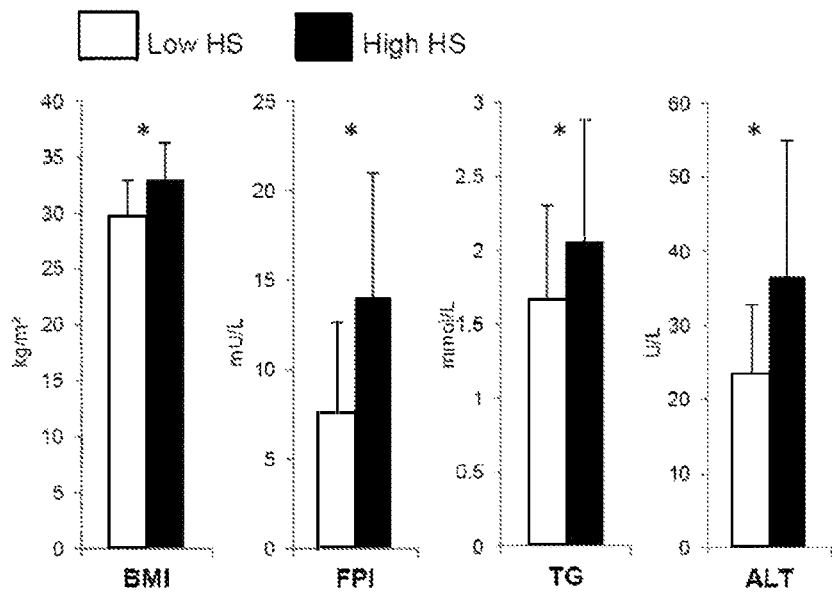

The subjects with varying degrees of HS were classified into two groups of 43 subjects based on their liver fat percentage: high HS (>5.5%) and low HS (<5.5%) (Table 1). It was found that subjects with high HS were significantly (P-value<0.05) heavier with a greater BMI. Fasting plasma glucose and fasting plasma insulin (FPI) concentrations were significantly (P-value<0.05) higher in subjects with high HS compared to subjects with low HS (FIG. 1B). The average plasma TG concentration was 2.05 mmol/L and 1.67 mmol/L for subjects with high and low HS, respectively (FIG. 1B). No significant plasma differences were detected in other lipid parameters including apoB, HDL cholesterol and total cholesterol (Table 1), The ALT level was significantly higher in subjects with high HS (FIG. 1B). In summary, the average subject with low HS involved in the study was overweight, borderline hypertriglyceridemic but insulin sensitive, whereas the average subject with high HS was obese, hypertriglyceridemic and insulin resistant but did not have T2D.

Personalized Liver Tissue GEMS

To elucidate the underlying molecular mechanisms of HS, constraint-based modeling techniques was adopted to identify major hepatic metabolic alterations between subjects with varying degrees of HS. The secretion rate of non-esterified fatty acids (FAs) and amino acids (AAs) from adipose and muscle tissues was calculated based on the body composition of each subject and used as an input to the personalized liver GEMs together with the lactate secreted by red blood cells, Since the level of TG-rich very low-density lipoproteins (VLDLs) is the major determinant of plasma TG, kinetic studies with stable isotopes and multi-compartment modeling were combined to infer the parameters of VLDL kinetics in 73 of the subjects (65 men and 8 women) involved in the study. A significant correlation between secreted VLDL and HS (r=0.581, P-value<0.001) was observed and secretion rate of VLDL was used as an objective function for the personalized liver GEMs.

Figure 2A:
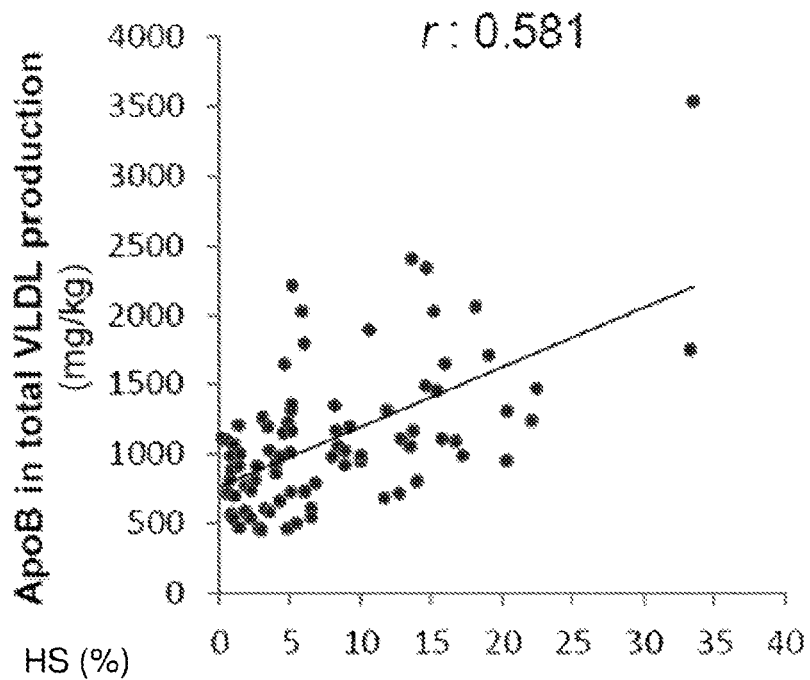
FIGS. 2A-2B: The correlation between the predicted intracellular fluxes of the liver and hepatic steatosis (HS) is assessed and compared with the A) apolipoprotein B (apoB) and B) triglycerides (TG) content in the total VLDL production.
Figure 2B:
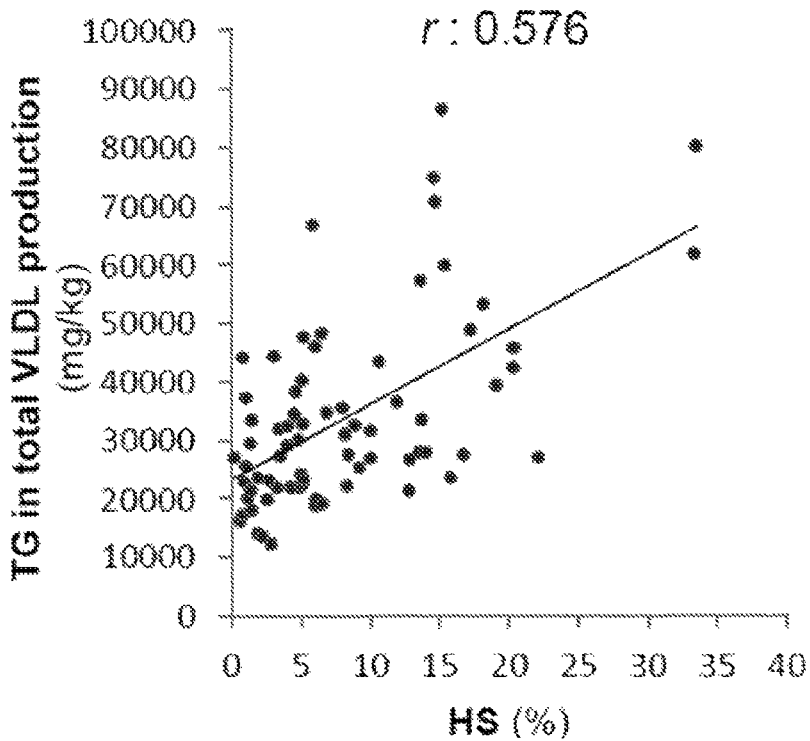

The desired dynamics of the liver metabolism to the increased HS was simulated using the inputs and outputs as constraints of personalized GEMs. The intracellular fluxes in the liver of each subject were predicted and Pearson correlation coefficient between the intracellular fluxes and HS of each subject was calculated. It was found that reactions involved in protein synthesis had the highest correlations with HS (r=0.57, P-value<0.001). The apoB content in the total VLDL produced by the liver was also quantified and it was found that it correlated significantly with the measured HS (r=P-value<0.001) (FIG. 2A). This correlation was very similar to that observed between the TG content in the total VLDL produced and the measured HS (r=0.576, P-value<0.001) (FIG. 2B). Hence, it was observed that personalized GEMs were able to predict the response of liver to the increased HS.

Reactions with the second and third highest correlations with HS were those involved in the reduction of $H_2O_2$ (r=0.482, P-value<0.001) and those associated with nicotinamide nucleotide transhydrogenase (NNT) (r=0.479, P-value<0.001), respectively. NNT catalyzes the interconversion of NADH and NADP+ to NAD+ and NADPH in the mitochondria, NNT has an important role in providing NAD+ for fat oxidation as well as NADPH for redox detoxification since NADPH is used for the regeneration of glutathione (GSH) through reduction of glutathione disulfide (GSSG), which is catalyzed by glutathione reductase (GSR). Notably, it was found that the flux carried by the reaction associated with GSR was one of those with the highest correlations with HS (r=0.478, P-value<0.001). Moreover, it was found that reactions involved in fat oxidation significantly correlated with HS (r=0.477, P-value<0.001). Increases in the flux carried by the reactions catalyzed by NNT and GSR would generate additional NAD+, which is necessary for the increased fat oxidation and GSH, which is necessary to scavenge excessively produced reactive oxygen species resulting from increased fat oxidation. It has previously been reported that NNT is essential for normal cellular metabolism and for mitochondrial defense against oxidative stress (Huang et al, 2006). In addition, a significant correlation was observed between HS and secreted ketone bodies, which are one of the major outputs of the liver GEM (r=0.475. P-value<0.001).

HS results from an imbalance between the de novo synthesis, oxidation, uptake and export of FAs (Tamura & Shimomura, 2005). Hence, the differences in the uptake and secretion rates of FAs, defined as net fat influx (NFI), in the liver of each subject were calculated and the correlations between the intracellular fluxes and NH were calculated. Notably, it was found that the reactions catalyzed by GSR (r=0.812, P-value<0.001) and NNT (r=0.811, P-value<0.001) had the highest correlations with NFL It was also found that the reaction catalyzed by glutathione peroxidases (GPXs) and peroxiredoxins (PRDXs), which detoxify peroxides and hydroperoxides, was significantly correlated with NFI (r=0.812, P-value<0.001). In addition, a significant correlation between NH and secreted ketone bodies (r=0.782, P-value<0.001) was observed.

The in silico analysis indicated that the increased HS can be compensated by the increased flux carried by the reactions that are catalyzed by NNT, GSR, GPXs and PRDXs in theory. However, the demand in the increase of the fluxes would not be met in practice and lead to increased HS in NAFLD patients. Considering that the simulations demonstrated the ideal response of the liver to the increased HS, the upregulation of the fat oxidation and the increased availability of the GSH may provides a treatment strategy for NAFLD subjects.

Glycine is the Limiting Substrate for De Novo Synthesis of GSH In NAFLD

Depletion of GSH can lead to mitochondrial dysfunction and cell death (Fernandez-Checa & Kaplowitz, 2005; Garcia-Canaveras et al, 2011). Based on the in silico analysis, it was proposed that increased expression of NNT may boost the level of NAD+ for the increased fat oxidation whereas NNT and GSR may boost the level of GSH required for resisting oxidative stress and maintaining the reducing environment of the liver. However, the expression of NNT and GSR could not continuously increase in vivo, which may result in depletion of NAD+ and GSH and eventually led to accumulation of fat in the liver. Indeed, hepatic depletion of NAD+ in mice model of NAFLD has been reported (Gariani et al, 2016; Zhou et al, 2016). Moreover, lower concentrations of both GSH and GSSG and a reduction in the GSH/GSSG ratio have been reported in the liver (Garcia-Canaveras et al, 2011) and serum (Kalhan et al, 2011) of NAFLD patients compared to healthy subjects.

Depleted GSH can also be replaced by de novo synthesis of GSH from glutamine, glycine and cysteine which can be taken up from the plasma. To detect the plasma level of these AAs, non-targeted metabolomics profiling in plasma from 86 subjects were performed and levels of ~520 metabolites were analyzed. The correlations between the plasma metabolite levels and HS were assessed. Fasting plasma levels of glycine and N-acetylglycine as well as betaine and serine (which can be converted to glycine) showed significantly negative correlations with HS. The correlation coefficients between the plasma metabolites that correlated significantly with HS were also assessed and it was found that plasma glycine levels showed the highest correlation with the plasma serine levels among all other measured metabolites (r=0.77, P-value<0.05). It should be noted that no significant correlation between HS and the plasma levels of cysteine and glutamine (which are also required for the de novo synthesis of GSH) was detected.

Figure 3:
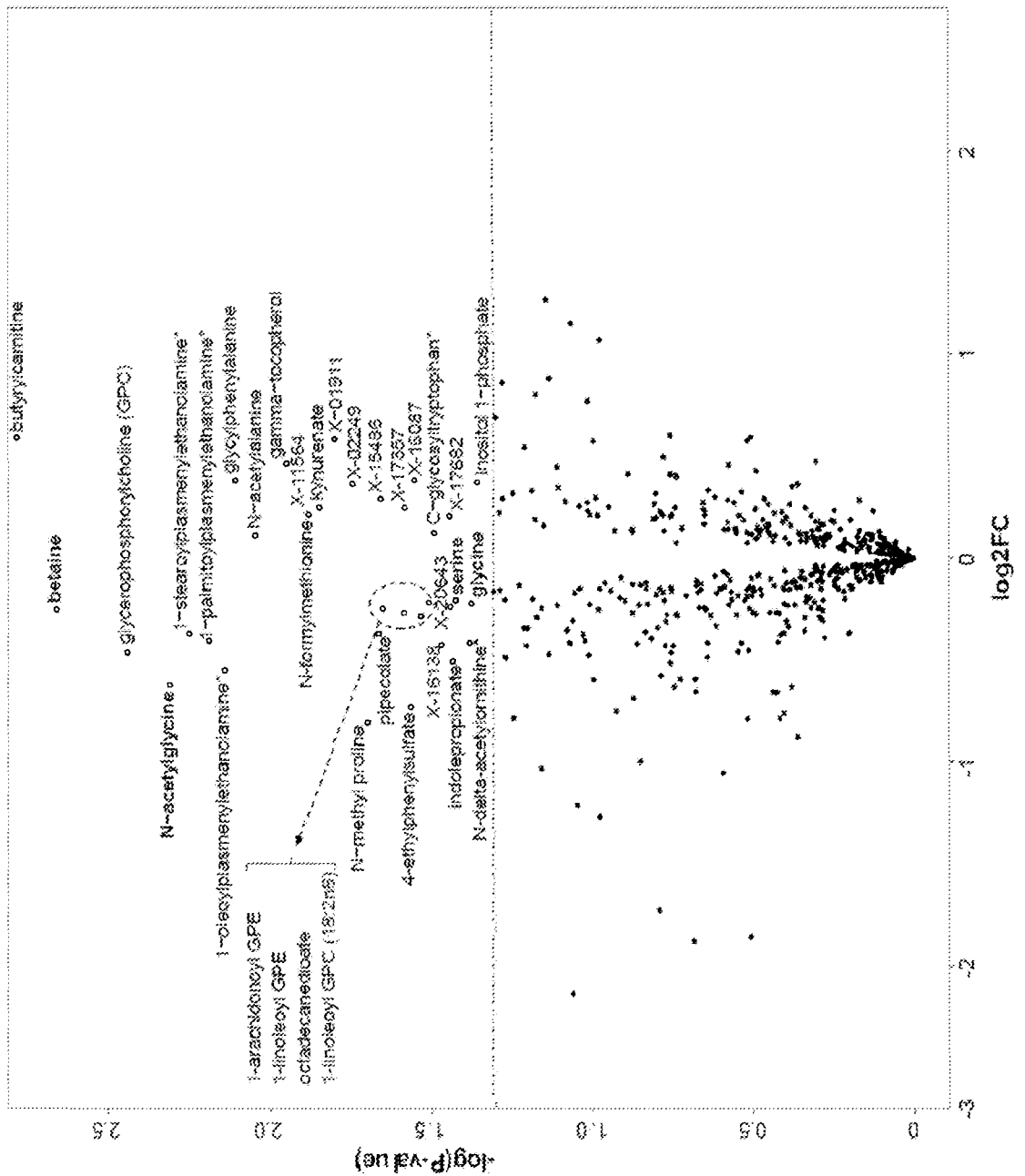
FIG. 3: Identification of significantly changed metabolites in subjects with high HS. The plasma level of ~520 metabolites was detected by untargeted metabolomics profiling and significantly (P-value<0.5) changed metabolites are presented using volcano plot.

It was also investigated if any of the plasma metabolites showed significant differences between the two groups of subjects divided according to their level of HS. It was found that the levels of glycine, serine, betaine and N-acetylglycine were significantly (Welsh's T-test, P-value<0.05) lower in subjects with high HS compared to those with low HS (FIG. 3). In addition to the metabolites associated with glycine, it was also found that the levels of butyrylcarnitine, glycylphenylalanine, gamma-tocopherol (vitamin E), kynurenate, N-delta-acetylornithine, N-methyl proline and a number of lipid structures that were shown to correlate with HS were significantly changed (Welsh's T-test, P-value<0.05) between the subjects with high and low HS (FIG. 3).

Decreased Expression of the Enzymes Involved in GSH Formation

Figure 4:
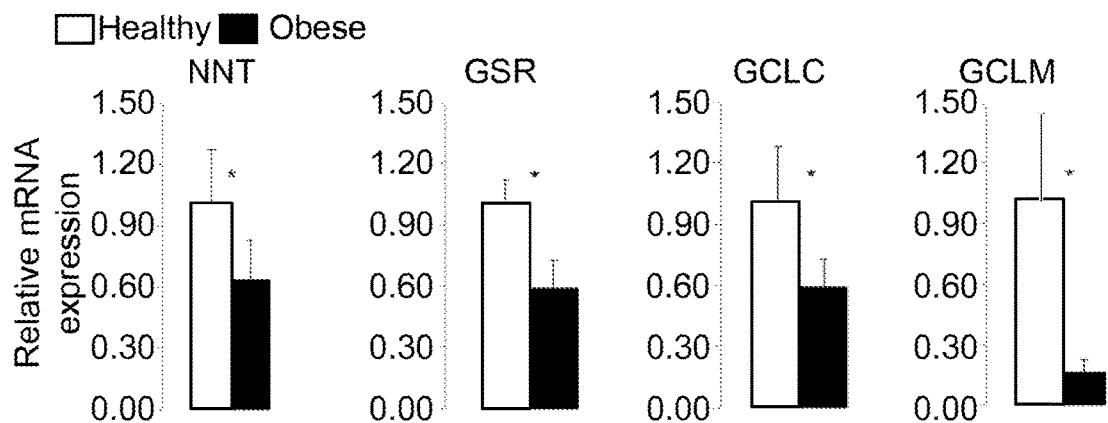
FIG. 4: The mRNA expressions of the nicotinamide nucleotide transhydrogenase (NNT), glutathione reductase (GSR), glutamate-cysteine ligase, catalytic subunit (GCLC) and glutamate-cysteine ligase, modifier subunit (GCLM) were measured in the liver obtained from 12 morbidly obese subjects underwent bariatric surgery and seven healthy individuals.

The critical role of GSH metabolism in the development of NAFLD was revealed. In this context, the expression of NNT, GSR and the enzymes involved in the de novo GSH synthesis in human liver samples obtained from a separate cohort of 12 obese subjects with high HS who underwent bariatric surgery (Table 2) was compared with liver samples obtained from seven healthy individuals (previously described in (Uhlen et al, 2015)). It was found that mRNA expression of NNT, GSR and the rate-limiting enzymes in de novo GSH synthesis, namely glutamate-cysteine ligase, catalytic subunit (GCLC) and glutamate-cysteine ligase, modifier subunit (GCLM), were significantly lower in liver from obese subjects than from healthy subjects (FIG. 4). This indicated that the decreased expression of the NNT and GSR may lead to increased HS which is in agreement with the results of personalized modeling of subjects with varying degree of HS.

Supplementation of GSH and NAD+ Precursors Decrease HS in Mice

The analysis indicated depletion of the NAD+ and GSH in subjects with high HS. It has been shown that supplementation of natural NAD+ precursors, such as nicotinamide riboside (NR), tryptophan, niacin, and nicotinamide elevates NAD+ levels in vivo (Canto et al, 2012; Houtkooper et al, 2010). The plasma and liver level of GSH is depleted in NAFLD patients and cannot be increased by supplementation with GSH; instead, GSH must be synthesized within the liver either de novo or by the salvation pathway. The analysis suggested that the level of GSH is not sufficient to maintain and regulate the thiol-redox status of the liver in subjects with high HS in the fasting state due to the depletion of glycine. Glycine can be synthesized via the interconversion of serine through serine hydroxymethyltransferases with concomitant conversion of tetrahydrofolate (THF) into 5,10-methylene-THF. During the conversion of serine to glycine, an additional carbon unit is provided for one-carbon metabolism. Taken together, it was hypothesized that dietary supplementation with NR may increase the level of NAD+ required for the increased fat oxidation and serine may increase the level of glycine and the level of GSH (by intracellular GSH synthesis from glycine). Supplementation of the substrates for NAD+ and GSH may increase the amount of the fat oxidized in the liver, lower oxidative stress resulting from high fat oxidation, lower the level of HS and eventually improve liver function.

Figure 5A:
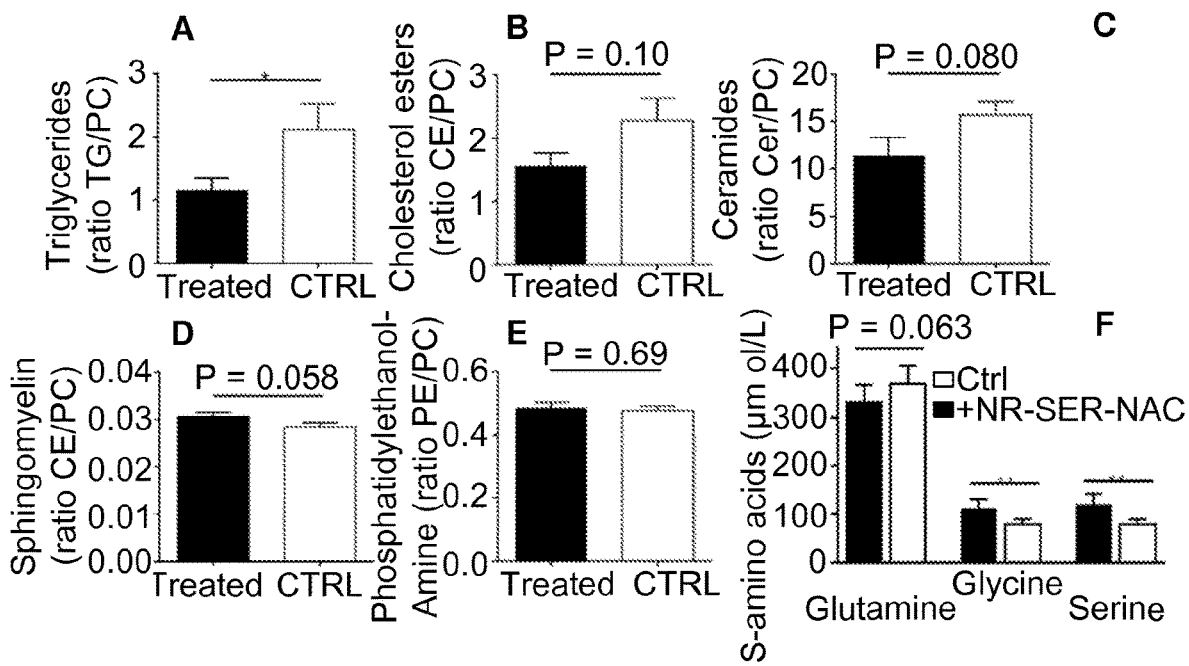
FIGS. 5A-5C: Supplementation of NAD+ and GSH precursors prevent NAFLD. 10 mice were treated with NR (400 mg/kg/day), serine (300 mg/kg/day) la gavage and 1 g/l of NAC (N-acetyl-L-cysteine) in the drinking water for 14 days.
Figure 5B:
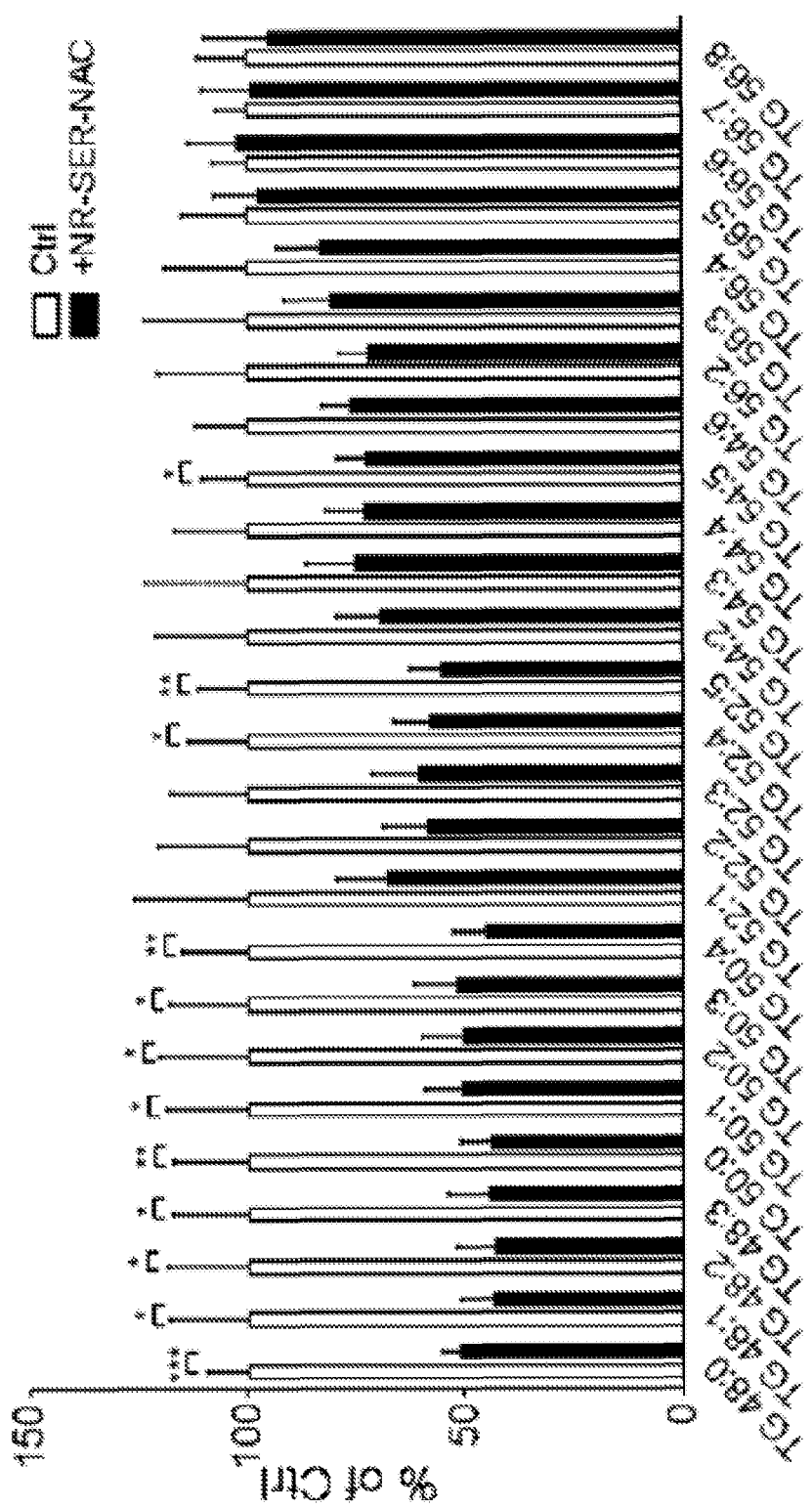

To assess the effect of GSH and NAD+ repletion on the development of HS in mice, a cocktail comprising serine, N-acetyl-L-cysteine (NAC) and NR was supplemented to mice fed with Western diet, including high levels of fat and sucrose. Serine was included in the cocktail since it can be easily converted to the glycine whereas NAC was included since cysteine may be the limiting metabolite after the repletion of the glycine in the synthesis of GSH. NR was included in the cocktail to increase the amount of NAD+ in the liver, Western diet fed Male C57BL/6N mice were treated with serine 300 mg/kg/day and NR 400 mg/kg/day la gavage as well as 1 g/l of NAC in the drinking water for 14 days and the mice were sacrificed 4 h after the last treatment, Liver lipidomics analysis was performed and the following was observed: a 50% reduction in hepatic TGs (FIG. 5A: panel A), a tendency to decrease in the level of cholesterol esters (FIG. 5A: panel B) and ceramides (FIG. 5A: panel C); a tendency to increase in the level sphingomyelin (FIG. 5A; panel D); and no significant changes in the level of phosphatidylethanolamine (FIG. 5A: panel E). The levels of glycine and serine were also measured, and it was found that their plasma levels were significantly increased after supplementation of the cocktail (FIG. 5A: panel F). Finally, the liver levels of TGs with different chain lengths were measured and it was found that the shorter chain lengths of TGs that are preferentially oxidized in the mitochondria were significantly decreased after supplementation (FIG. 5B: panel G). Hence, it has been demonstrated that supplementation of the metabolites that were predicted by personalized modeling promotes the oxidation of fat in the liver and prevents HS. Accordingly, the mice study confirmed the proposed therapeutic strategy for protection against NAFLD progression.

Supplementation of Serine Decreases HS in Humans

Figure 5C:
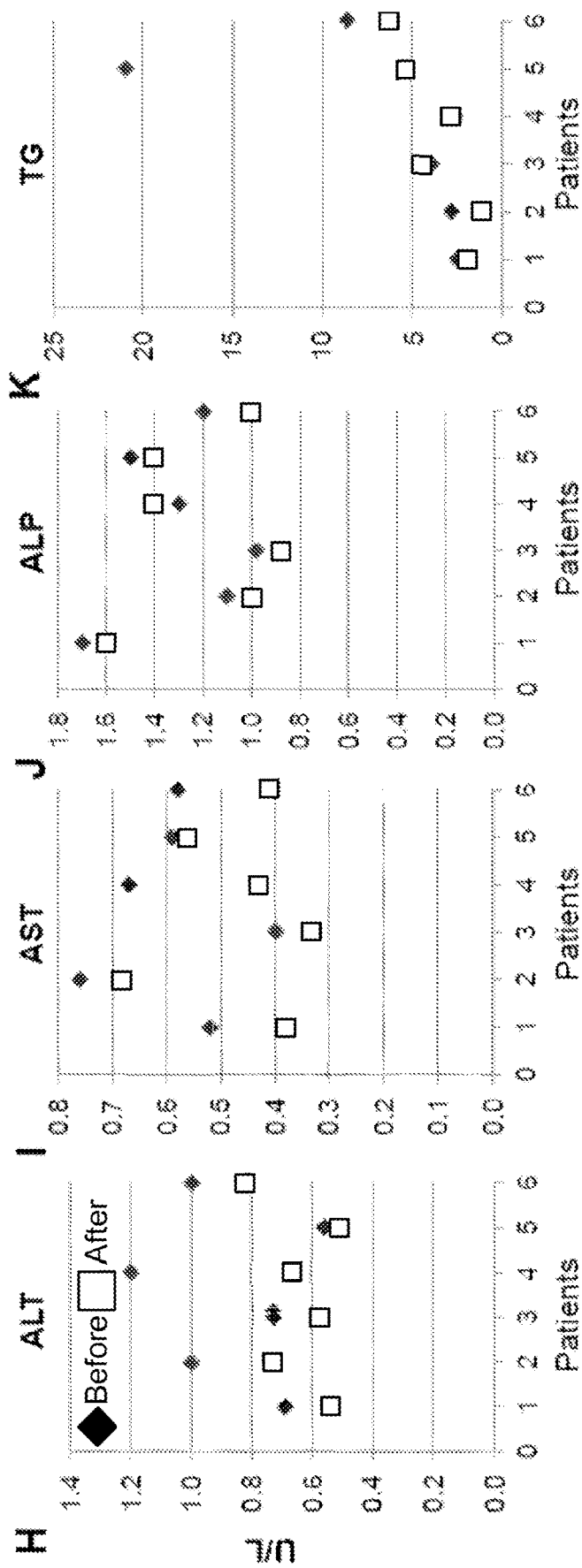

To identify the unique contribution of serine supplementation in decreasing HS, the effect of short-term dietary supplementation with serine on HS and fasting levels of plasma markers of liver functions was assessed in six subjects with high HS. Characteristics of the six subjects before and after the supplementation are presented in Table 3. Each patient received one oral dose of ~20 g of L-serine (200 mg/kg) per day for 14 days. The supplementation was well tolerated by all the subjects. It was found that the plasma level or serine is significantly increased and that the plasma levels of ALT, AST and ALP were significantly decreased after supplementation (Table 3). Notably, it was found that the plasma levels of ALT (FIG. 5C: panel H) and AST (FIG. 5C: panel I) were consistently decreased in all six subjects and ALP was decreased in five of the participating subjects (FIG. 5C: panel J). Moreover, it was found that the plasma TGs were decreased in five of the studied subjects and did not change in the remaining one subject (FIG. 5C: panel K). The HS was also measured using magnetic resonance spectroscopy before and after serine supplementation and it was demonstrated that HS is significantly decreased after serine supplementation (Table 3). HS is decreased in all six patients and the relative decrease in NAFLD patients ranged between 1.0-23%.

CALIBRATION STUDY

Nine (9) healthy subjects (BMI<30) were recruited. Hence, the recruited subjects did not suffer from T2D or NAFLD and were not on any medication. All subjects entering into the study had signed informed consent form.

The subjects stayed at the same hotel and had the same breakfast and lunch during the study. This allowed for monitoring possible side effects of the medicinal product.

The study started at 08:00 every day and supplementation was carried out as follows:

On day 1, each subject received one oral dose of 1 g (0.0039 mol) of NR.

On day 2, each subject received one oral dose of 3 g (0.019 mol) of L-carnitine

On day 3, each subject received one oral dose of 5 g (0.031 mol) of NAC.

On day 4, each subject received one oral dose of a complete medicinal product, in this case 1 g of NR, 3 g of L-carnitine, 5 g of NAC and 20 g of L-serine.

On day 5, each subject received one oral dose of 20 g (0.19 mol) of L-serine.

In the complete medicinal product, the molar ratio of serine to NR was thus about 48:1, the molar ratio of serine to NAC was about 6.1:1 and the molar ratio of serine to L-carnitine was about 10:1.

Blood samples were collected before (08:00) and after (12:00) supplementation on day 1, 2, 3 and 5.

Blood samples were collected eight (8) times (08:00, 09:00, 10:00, 11:00, 12:00, 13:00, 14:00 and 15:00) on day 4 (to understand the kinetics of all medicinal product substances).

A glucose monitoring device was used to measure the glucose level of the subjects during the study.

The plasma level of glucose, insulin, gamma GT, bilirubin, ALP, ASAT, ALAT, FFAs, TAGs, Total cholesterol, HDL and LDL was measured before and after supplementation.

Plasma levels of serine, L-carnitine, NAC and NAD+ were measured using targeted metabolomics platform.

No subject was withdrawn from the study and no side effect has been reported.

It has been observed that the serine plasma level of diseased patients is about 50% of that of healthy subjects. Therefore, it was desired to find an oral serine dose that results in a one-fold increase of the plasma serine level. Further, a one-fold increase of the plasma serine level was expected to reflect a significant increase of the liver serine level. As discussed above under SUMMARY, cysteine becomes limiting for the formation of the antioxidants after sufficient supplementation with serine (or glycine). Accordingly, it was also desired to find an oral NAC dose that results in a one-fold increase of the plasma NAC level. Finally, it was desired to find an oral L-carnitine dose that results in a one-fold increase of the plasma L-carnitine level, which follows from the above discussion under SUMMARY.

A three-compartment ordinary differential equation (ODE) model that represents the stomach, intestine and the blood was developed based on public information. The model was fitted to the experimentally measured plasma concentrations. One model for each of serine, L-carnitine and NAC was thus developed based on the average plasma concentration of the substance in question in the subjects over the course of up to 24 hours after ingestion. Bioavailability of each substance was set according to literature values.

Interpolations of the plasma concentrations of each substance were constructed for each subject. The mean of the interpolations was used as the target concentration curve. The model was subsequently fitted to this curve. Once the model was fitted to each substance, the model was used to predict the resulting plasma concentration when subject to a twice-daily supplementation regimen. The individual dosages of the substances were adjusted to achieve the desired 100% increase in average (long term) plasma concentration without superseding safe doses for human consumption.

The model predicted that a twice-daily dose of 12.75 g (0.121 mol) of serine will produce the desired long term increase in mean plasma serine concentration of 100%. Such a twice-daily dose corresponds to 3.5 mmol/kg/day of serine in case of a 70 kg patient. Doses up to 400 mg/kg/day (around 25-30 g/day) have been studied in humans and shown to be safe.

Regarding L-carnitine, the model predicted that a twice-daily dose of 8.2 g (0.0509 mol) L-carnitine will produce the desired long term increase in mean plasma L-carnitine concentration of 100%. However, since long term supplementation studies for the safety of L-carnitine above 7 g (0.0434 mol) per day have not been examined, the recommended dose was lowered to 3 g (0.0186 mol) twice-daily. This resulted in a long-term increase in mean plasma concentration of 37%, which was considered a reasonable trade-off between risk of toxicity and increase in plasma concentration. The twice-daily dose of 3 g of L-carnitine corresponds to 0.53 mmol/kg/day of L-carnitine in case of a 70 kg patient.

Regarding NAC, the model predicted that a twice-daily dose of 3.2 g (0.0196 mol) of NAC will produce the desired long term increase in mean plasma NAC concentration of 100%. Such a twice-daily dose corresponds to 0.56 mmol/kg/day of serine in case of a 70 kg patient. A daily dosage of 4-6 grams of NAC has been shown to be safe in humans.

Trammell et al (2016) supports continued use of a twice-daily dose of 1 g (0.0039 mol) of NR. Such a twice-daily dose corresponds to 0.11 mmol/kg/day of NR in case of a 70 kg patient.

In the adjusted complete medicinal product, the molar ratio of serine to NR was thus about 31:1, the molar ratio of serine to NAC was about 6.2:1 and the molar ratio of serine to L-carnitine was about 6.5:1.

REFERENCES

Adiels M, Packard C, Caslake M J, Stewart P, Soro A, Westerbacka J, Wennberg B, Olofsson S O, Taskinen M R, Boren J (2005) A new combined multicompartmental model for apolipoprotein B-100 and triglyceride metabolism in VLDL subfractions. *J Lipid Res* 46: 58-67

Adiels M, Taskinen M R, Packard C, Caslake M J, Soro-Paavonen A, Westerbacka J, Vehkavaara S, Hakkinen A, Olofsson S O, Yki-Jarvineri H, Boren J (2006) Overproduction of large VLDL particles is driven by increased liver fat content in man. *Diabetologia* 49: 755-765

Ardilouze J L, Fielding B A, Currie J M, Frayn K N, Karpe F (2004) Nitric oxide and beta-adrenergic stimulation are major regulators of preprandial and postprandial subcutaneous adipose tissue blood flow in humans. *Circulation* 109: 47-52

Benga G, Ferdinand W (1995) Amino acid composition of rat and human liver microsomes in normal and pathological conditions. *Biosci Rep* 15: 111-116

Bickerton A S T, Roberts R, Fielding B A, Hodson L, Blaak E E, Wagenmakers A J M, Gilbert M, Karpe F, Frayn K N (2007) Preferential uptake of dietary fatty acids in adipose tissue and muscle in the postprandial period. *Diabetes* 56: 168-176

Bourre J M (2006) Effects of nutrients (in food) on the structure and function of the nervous system: update on dietary requirements for brain. Part 2: macronutrients, *J Nutr Health Aging* 10: 386-399

Canto C, Houtkooper R H, Pirinen E, Youn D Y, Oosterveer M H, Cen Y, Fernandez-Marcos P J, Yamamoto H, Andreux P A, Cettour-Rose P, Gademann K, Rinsch C, Schoonjans K, Sauve A A, Auwerx J (2012) The NAD(+) precursor nicotinamide riboside enhances oxidative metabolism and protects against high-fat diet-induced obesity. *Cell Metab* 15: 838-847

Clark R V, Walker A C, O'Connor-Semmes R L, Leonard M S, Miller R R, Stimpson S A, Turner S M, Ravussin E, Cefalu W T, Hellerstein M K, Evans W J (2014) Total body skeletal muscle mass: estimation by creatine (methyl-d3) dilution in humans. *J Appl Physiol* 116: 1605-1613

Cuervo A M, Dice J F (1996) A receptor for the selective uptake and degradation of proteins by lysosomes. *Science* 273: 501-503

Deureaiberg P, Weststrate J A, Seidel J C (1991) Body-Mass Index as a Measure of Body Fatness—Age-Specific and Sex-Specific Prediction Formulas. *Brit J Nutr* 65: 105-114

Dyson J K, Anstee Q M, McPherson S (2014) Non-alcoholic fatty liver disease: a practical approach to treatment. *Frontline Gastroenterol* 5: 277-286

Fernandez-Checa J C, Koplowitz N (2005) Hepatic mitochondrial glutathione: transport and role in disease and toxicity. *Toxicol Appl Pharmacol* 204: 263-273

Frayn K N, Karpe F (2014) Regulation of human subcutaneous adipose tissue blood flow. *Int J Obesity* 38: 1019-1026

Garcia-Canaveras J C, Donato M T, Castel J V, Lahoz A (2011) A comprehensive untargeted metabonomic analysis of human steatotic liver tissue by RP and HILIC chromatography coupled to mass spectrometry reveals important metabolic alterations. *J Proteome Res* 10: 4825-4834

Gariani K, Menzies K J, Ryu D, Wegner C J, Wang X, Ropelle E R, Moullan N, Zhang H, Perino A, Lernos V, Kim B, Park Y K, Piersigilli A, Phalli T X, Yang Y, Ku C S, Kao S I, Fomitchova A, Canto C, Schoonjans K et al (2016) Eliciting the mitochondrial unfolded protein response h nicotinamide adenine dinucleotide repletion reverses fatty liver disease in mice. *Hepatology* 63: 1190-1204

Hellerstein M K, Neese R A, Linfoot P, Christiansen M, Turner S, Letscher A (1997) Hepatic gluconeogenic fluxes and glycogen turnover during fasting in humans. A stable isotope study. *The Journal of clinical investigation* 100: 1305-1319

Houtkooper R H, Canto C, Wanders R J, Auwerx J (2010) The secret life of NAD+: an old metabolite controlling new metabolic signaling pathways. *Endocr Rev* 31: 194-223

Huang T T, Naeemuddin M, Elchuri S, Yamaguchi M, Kozy H M, Carlson E J, Epstein C J (2006) Genetic modifiers of the phenotype of mice deficient in mitochondrial superoxide dismutase. *Hum Mol Genet* 15: 1187-1194

Kalhan S C, Guo L N, Edmison J, Dasarathy S, McCullough A J, Hanson R W, Milburn M (2011) Plasma metabolomic profile in nonalcoholic fatty liver disease. *Metabolism* 60: 404-413

Karpe F, Dickmann J R, Frayn K N (2011) Fatty acids, obesity, and insulin resistance: time for a reevaluation. *Diabetes* 60: 2441-2449

Lofgren L, Stahlman M, Forsberg G B, Saarinen S, Nilsson R, Hansson G I (2012) The BUME method: a novel automated chloroform-free 96-well total lipid extraction method for blood plasma. *J Lipid Res* 53: 1690-1700

Lundbom J, Hakkarainen A, Soderlund S, Westerbacka J, Lundbom N, Taskinen R (201) Long-TE H-1 MRS suggests that liver fat is more saturated than subcutaneous and visceral fat. *NMR Biomed* 24: 238-245

Machado M V, Cortez-Pinto H (2012) Non-Invasive Diagnosis of Non-Alcoholic Fatty Liver Disease—A Critical Appraisal. *J Hepatol* 58: 1007-1019

Mardinoglu. A, Agren R, Kampf C, Asplund A, Uhlen M, Nielsen J (2014) Genome-scale metabolic modelling of hepatocytes reveals serine deficiency in patients with non-alcoholic fatty liver disease. *Nat Commun* 5: 3083

Mardinoglu A, Nielsen. J (2015) New paradigms for metabolic remodeling of human cells. *Curr Opin Biotech* 34: 91-97

Mardinoglu A, Shoaie S, Bergentall M, Ghaffari P, Zhang C, Larsson E, Bäckhed F, Nielsen J (2015b) The gut microbiota modulates host amino acid and glutathione metabolism in mice *Mol Syst Biol* 11: 834

McQuaid S E, Hodson L, Neville M J. Dennis A L, Cheeseman J, Humphreys S M, Ruge T, Gilbert M, Fielding B A, Frayn K N, Karpe F (2011) Downregulation of Adipose Tissue Fatty Acid Trafficking in Obesity A Driver for Ectopic Fat Deposition? *Diabetes* 60: 47-55

Nestel P J, Whyte H M (1968) Plasma free fatty acid and triglyceride turnover in obesity. *Metabolism: clinical and experimental* 17: 1122-1128

Norrelund H, Nair K S, Jorgensen J O, Christiansen J S, Moller N (2001) The protein-retaining effects of growth hormone during fasting involve inhibition of muscle-protein breakdown, *Diabetes* 50: 96-104

Patterson B W, Horowitz J F, Wu G Y, Watford M, Coppack S W, Klein S (2002) Regional muscle and adipose tissue amino acid metabolism in lean and obese women. *Am J Physiol-Endoc M* 282: E931-E936

Pozefsky T, Tancredi R G, Moxley R T, Dupre J, Tobin J D (1976) Effects of brief starvation on muscle amino acid metabolism in nonobese man. *The Journal of clinical investigation* 57: 444-449

Ratziu V, Bellentani S, Cortez-Pinto H, Day C, Marchesini G (2010) A position statement on NAFLD/NASH based on the EASL 2009 special conference. *J Hepatol* 53: 372-384

Reichard G A, Jr., Owen O E, Haff A C, Paul P, Bortz W M (1974) Ketone-body production and oxidation in fasting obese humans. *The Journal of clinical investigation.* 53: 508-515

Stahlman M, Fagerberg B, Adiels M, Ekroos K, Chapman J M, Kontush Boren J (2013) Dyslipidernia, but not hyperglycemia and insulin resistance, is associated with marked alterations in the HDL lipidome in type 2 diabetic subjects in the DIVA cohort: impact on small HDL particles. *Biochem Biophys Acta* 1831:1609-1617

Tamura S, Shimomura I (2005) Contribution of adipose tissue and de novo lipogenesis to nonalcoholic fatty liver disease. *The Journal of clinical investigation* 115: 1139-1142

Trammell, S, Schmidt, M, Weidemann, B, Redpath, P, Jaksch, F, & Dellinger, R et al, (2016) Nicotinamide riboside is uniquely and orally bioavailable in mice and humans. *Nature Communications* 7:12948.

Uhlen M, Fagerberg L, Hallstrom B M, Lindskog C, Oksvold P, Mardinoglu A, Sivertsson A, Kampf C, Sjöstedt E, Asplund A, Lundberg E, Djureinovic D, Odeberg J, Habuka M, Tahmasebpoor S, Danielsson A, Edlund K, Szigyarto C A, Skogs M, Takanen J O et al (2015) Tissue-based map of the human proteome. *Science* 347: 1260419

Vetelainen R, van Vliet A, Gouma D J, van Gulik T M (2007) Steatosis as a risk factor in liver surgery. *Ann Surg* 245: 20-30

Wallace J C (2002) *Gluconeogenesis. Encyclopedia of Life Sciences.*

Zhou C C, Yang X, Hua X, Liu J, Fan M B, Li G Q, Song J, Xu T Y, Li Z Y, Guan Y F, Wang P, Miao C Y (2016) Hepatic NAD(+) deficiency as a therapeutic target for non-alcoholic fatty liver disease in ageing. *Brit J Pharmacol* 173: 2352-2368

The invention claimed is:

1. A composition comprising:
   A) serine, betaine, and/or glycine;
   B) N-acetyl cysteine and/or cysteine;
   C) L-carnitine; and
   D) nicotinamide riboside and/or nicotinamide,
wherein the molar ratio of A) to D) is between 50:1 and 3:1 and the molar ratio of A) to B) is between 16:1 and 1.5:1.

2. The composition of claim 1, wherein the substances included in groups A)-D) amount to at least 25% of the dry weight of the composition.

3. The composition of claim 1, wherein the substances included in groups A)-D) amount to at least 50% of the dry weight of the composition.

4. The composition of claim 1, which is a solid.

5. The composition of claim 4, which is a solid powder.

6. The composition of claim 5, wherein the powder is packaged and the pack of powder comprises 48-478 mmol of A) and/or 2.0-39.2 mmol of D) when D) is nicotinamide riboside and 2.0-196 mmol of D) when D) is nicotinamide.

7. A method of treating a medical condition in a subject, comprising administering the composition of claim 1 to the subject.

8. The method of claim 7, wherein the composition is administered orally.

9. The method of claim 8, wherein said method comprises oral administration of:
   A) in a dose of 0.48-24 mmol/kg/day;
   B) in a dose of 0.31-3.05 mmol/kg/day;
   C) in a dose of 0.031-1.24 mmol/kg/day; and
   D) in a dose of 0.020-0.39 mmol/kg/day when D) is nicotinamide riboside and 0.0196-1.96 mmol/kg/day when D) is nicotinamide.

10. The method of claim 9, wherein said method comprises oral administration of:
    A) in a dose of 0.48-4.8 mmol/kg/day.

11. The method of claim 10, wherein said method comprises oral administration of:
    A) in a dose of 1.8-4.8 mmol/kg/day.

12. The method of claim 9, wherein said method comprises oral administration of:
    D) in a dose of 0.039-0.31 mmol/kg/day.

13. The method of claim 7, wherein the medical condition is selected from the group consisting of non-alcoholic fatty liver disease (NAFLD), alcoholic fatty liver disease (AFLD), type 2 diabetes, obesity, insulin resistance, and dyslipidemia.

14. The method of claim 13, wherein the medical condition is non-alcoholic steatohepatitis (NASH).

15. A method of treating a medical condition in a subject, comprising simultaneous, separate or sequential administration to the subject of
    A) serine, betaine, and/or glycine,
    B) N-acetyl cysteine and/or cysteine,
    C) L-carnitine; and
    D) nicotinamide riboside and/or nicotinamide,
wherein the molar ratio of A) to D) is between 50:1 and 3:1 and the molar ratio of A) to B) is between 16:1 and 1.5:1.

16. The method of claim 15, wherein the medical condition is selected from the group consisting of non-alcoholic fatty liver disease (NAFLD), alcoholic fatty liver disease (AFLD), type 2 diabetes, obesity, insulin resistance and dyslipidemia.

17. The method of claim 16, wherein the medical condition is non-alcoholic steatohepatitis (NASH).

18. The composition of claim 1, wherein the composition comprises:
    A) serine;
    B) N-acetyl cysteine;
    C) L-carnitine; and
    D) nicotinamide.

19. The composition of claim 1, wherein the composition comprises:
    A) serine;
    B) cysteine;
    C) L-carnitine; and
    D) nicotinamide.

20. The composition of claim 1, wherein the composition comprises:
    A) serine;
    B) N-acetyl cysteine;
    C) L-carnitine; and
    D) nicotinamide riboside.

21. The composition of claim 1, wherein the composition comprises:
    A) betaine;
    B) N-acetyl cysteine;
    C) L-carnitine; and
    D) nicotinamide riboside.

* * * * *

UNITED STATES PATENT AND TRADEMARK OFFICE
CERTIFICATE OF CORRECTION

PATENT NO.         : 11,813,236 B2
APPLICATION NO.    : 17/471780
DATED              : November 14, 2023
INVENTOR(S)        : Mardinoglu et al.

It is certified that error appears in the above-identified patent and that said Letters Patent is hereby corrected as shown below:

In the Specification

Column 1, Line 28: Please correct "(T21))" to read --(T2D)--

Column 2, Line 27: Please correct "NAD" to read --NAD+--

Column 2, Line 35: Please correct "THE It" to read --THF. It--

Column 4, Line 43: Please correct "ITS" to read --HS--

Column 5, Line 21: Please correct "between and 3:1" to read --between 10:1 and 3:1--

Column 6, Lines 50-51: Please correct "gamma-butyrobetaine, trimethylammoniobutanal" to read --gamma-butyrobetaine, 4-trimethylammoniobutanal--

Column 7, Line 63: Please correct "96" to read --%--

Column 8, Line 64: Please correct "ITS" to read --HS--

Column 9, Line 60: Please correct "mmol/mi" to read --mmol/ml--

Column 12, Line 23: Please correct "swine" to read --serine--

Column 12, Lines 27-28: Please correct "gamma-butyrobetaine, trimethylammoniobutanal" to read --gamma-butyrobetaine, 4-trimethylammoniobutanal--

Column 12, Line 53: Please correct "HIS" to read --HS--

Column 14, Line 55: Please correct "(R→2=0.69)" to read --(R^2=0.69)--

Signed and Sealed this
Twenty-seventh Day of February, 2024

Katherine Kelly Vidal
*Director of the United States Patent and Trademark Office*

CERTIFICATE OF CORRECTION (continued)
U.S. Pat. No. 11,813,236 B2

Column 15, Line 37: Please correct "PMI" to read --BMI--

Column 15, Lines 39-40: Please correct "gender is for" to read --gender is 0 for--

Column 18, Line 3: Please correct "(30 mg/kg)" to read --(300 mg/kg)--

Column 18, Line 6: Please correct "Ali" to read --All--

Column 19, Line 40: Please correct "(r=P-value<0.001)" to read --(r=0.581, P-value<0.001)--

Column 20, Line 11: Please correct "NH" to read --NFI--

Column 20, Line 14: Please correct "NFL It" to read --NFI. It--

Column 20, Line 19: Please correct "NH" to read --NFI--

Column 25, Line 22: Please correct "Deureaiberg" to read --Deurenberg--